US010005757B2

(12) United States Patent
Liu et al.

(10) Patent No.: US 10,005,757 B2
(45) Date of Patent: Jun. 26, 2018

(54) REVAPRAZAN HYDROCHLORIDE POLYMORPHS AND PREPARATION METHOD THEREFOR

(71) Applicant: JIANGSU TASLY DIYI PHARMACEUTICAL CO., LTD., Jiangsu (CN)

(72) Inventors: Wenzheng Liu, Jiangsu (CN); Guocheng Wang, Jiangsu (CN); Qingwei Hou, Jiangsu (CN); Hongguang Meng, Jiangsu (CN)

(73) Assignee: Jiangsu Tasly Diyi Pharmaceutical Co., Ltd., Jiangsu (CN)

( * ) Notice: Subject to any disclaimer, the term of this patent is extended or adjusted under 35 U.S.C. 154(b) by 0 days. days.

(21) Appl. No.: 15/520,290

(22) PCT Filed: Nov. 12, 2015

(86) PCT No.: PCT/CN2015/094463
§ 371 (c)(1),
(2) Date: Apr. 19, 2017

(87) PCT Pub. No.: WO2016/078543
PCT Pub. Date: May 26, 2016

(65) Prior Publication Data
US 2017/0334877 A1    Nov. 23, 2017

(30) Foreign Application Priority Data
Nov. 19, 2014 (CN) .......................... 2014 1 0665192

(51) Int. Cl.
*C07D 401/04* (2006.01)
(52) U.S. Cl.
CPC ........ *C07D 401/04* (2013.01); *C07B 2200/13* (2013.01)
(58) Field of Classification Search
CPC .................................................. C07D 401/04
See application file for complete search history.

(56) References Cited

U.S. PATENT DOCUMENTS

| 5,750,531 | A | * | 5/1998 | Lee | ...................... | C07D 401/04 |
| | | | | | | 514/256 |
| 5,990,311 | A | | 11/1999 | Hong et al. | | |
| 6,252,076 | B1 | * | 6/2001 | Hong | ................... | C07D 217/02 |
| | | | | | | 544/321 |

FOREIGN PATENT DOCUMENTS

| CN | 1217722 A | 5/1999 | | |
| WO | 9605177 A1 | 2/1996 | | |
| WO | 9742186 A1 | 11/1997 | | |
| WO | 9818784 A1 | 5/1998 | | |
| WO | WO-9818784 A1 * | 5/1998 | .......... | C07D 217/02 |
| WO | WO-02088088 A1 * | 11/2002 | .......... | C07D 211/29 |
| WO | 2014/060908 A1 | 4/2014 | | |
| WO | WO-2014060908 A1 * | 4/2014 | .......... | C07D 401/04 |

OTHER PUBLICATIONS

Ding, Bing, "Study on the Synthesis of the Reversible Proton Pump Inhibitor Revaprazan Hydrochloride", Medicine & Public Health, China Master's Theses Full-Text Database, Jul. 31, 2010 (Jul. 31, 2010) p. 16, section 2.5 and pp. 37-39, section 5.3 (translation of pertinent section only provided).
Song, Wei-guo et al., "A New Method for Preparing Revaprazan Hydrochloride". Chinese Journal of New Drugs 2013, 22(14), 1694-1696 (translation of pertinent section only provided).
Sun, Zheng-jin et al., "Synthesis of Revaprazan Hydrochloride", Chinese Journal of Pharmaceuticals, vol. 39, No. 5,May 31, 2008, see the whole document (translation of pertinent section only provided).
Jiang, Jun-rong et al., "Synthesis of Revaprazan"; Journal of Synthetic Chemistry 2008, 16(4), 490-492 (translation of pertinent sector provided).
Ding, Bing et al; "Synthesis of 4-hydroxy-2-(4-fluoroanilino)-5,6-dimethylpyryimidine"; Journal of Guongdong Pharmaceutical University, Apr. 2009, 25(2), 173-174 (translation of pertinent section provided).
Merck indexing of Revaprazan Hydrochloride, 2013, last revised.
International Search Report from International Application No. PCT/CN2015/094462 dated Feb. 16, 2016.

* cited by examiner

*Primary Examiner* — Alexander R Pagano
*Assistant Examiner* — Ebenezer O Sackey
(74) *Attorney, Agent, or Firm* — Dilworth & Barrese, LLP

(57) ABSTRACT

Provided are revaprazan hydrochloride polymorphs and a preparation method thereof. The method comprises a step of dissolving revaprazan hydrochloride in ethanol or aqueous solutions of ethanol having different proportions to perform recrystallization.

23 Claims, 10 Drawing Sheets

Fig. 4

REVAPRAZAN HYDROCHLORIDE POLYMORPHS AND PREPARATION METHOD THEREFOR

TECHNICAL FIELD

The present invention belongs to the field of pharmaceuticals, relates to pharmaceutical compound crystalline forms and preparation methods thereof, and particularly relates to a reversible proton pump inhibitor pharmaceutical revaprazan hydrochloride polymorph and a preparation method thereof.

BACKGROUND ART

Revaprazan hydrochloride is a new generation of reversible proton pump inhibitor, and also is the world's only marketed potassium competitive acid pump inhibitor. Since the onset of effect is rapid, generally achieving maximum plasma concentration at about 1 h, revaprazan hydrochloride is used for rapid relief of symptoms caused by gastric acid. And it has clinical significance in meeting treatment demand and controlling gastrointestinal bleeding of patients. Its efficacy has a linear relationship with the oral dosage, which means that the gastric acid can be controlled at the best level by adjusting pharmaceutical dosage, thus meeting individualized treatment of different patients. It is used for treating peptic ulcer and other diseases relating to excessive secretion of gastric acid.

Revaprazan hydrochloride was marketed in 2007. Although there are several documents reporting its synthesis process, the reports about a refining method and crystalline forms of revaprazan hydrochloride have not been seen. Document (WO9742186; WO9818784; *Chinese Journal of Pharmaceuticals* 2008, 39 (5), 321-324; *Chinese Journal of Synthetic Chemistry* 2008, 16 (4), 490-492; *Chinese Journal of New Drugs* 2013, 22 (14), 1694-1696) reported that the melting point of revaprazan hydrochloride is 255-256° C., while WO9605177 and MERCK indexing reported that the melting point of revaprazan hydrochloride is 205-208° C. We studied its refining method and crystalline forms, and found that recrystallizing the revaprazan hydrochloride using ethanol aqueous solutions with different proportions could obtain products exhibiting different crystalline forms, and the melting point is between 210-226° C.

SUMMARY OF THE INVENTION

To solve the above technical problems, the present invention provides a revaprazan hydrochloride polymorph which particularly comprises 5 crystalline forms.

The present invention also provides a preparation method of above-mentioned 5 crystalline forms.

Disclosed is a revaprazan hydrochloride polymorph of the present invention, characterized in that its melting point is 210-226° C.

Disclosed is also a revaprazan hydrochloride crystalline form I, the melting point of the polymorph I being 221-226° C.

In the powder X-ray diffraction pattern of the crystalline form I, 2θ, which is represented in degree with the characteristic diffraction peaks at 10.24±0.2, 21.92±0.2, 17.54±0.2, 26.70±0.2, and 20.72±0.2.

The powder X-ray diffraction peaks of further preferred crystalline form I are shown in Table 21. The thermogravimetric-differential thermal analysis atlas TG-DTA of the crystalline form I shows that there is an endothermic peak at 223° C.

The infra-red spectrogram of the crystalline form I shows that there are characteristic absorption peaks at 3429.20, 3263.33, 2979.82, 2914.24, 1643.24, 1633.59, 1583.45, 1504.37, 1434.94, 1413.72, 1340.43, 1303.79, 1218.93, 1155.28, 1114.78, 1064.63, 1039.56, 972.06, 862.12, 833.19, 773.40, 757.97, and 514.96 cm$^{-1}$.

Disclosed is also a revaprazan hydrochloride crystalline form II of the present invention, the melting point of the crystalline form II being 218-222° C.

In the powder X-ray diffraction pattern of the polymorph II, 2θ, which is represented in degree with the characteristic diffraction peaks at 0.26±0.2, 24.48±0.2, 7.62±0.2, 21.94±0.2, 26.76±0.2, and 28.00±0.2.

The powder X-ray diffraction peaks of further preferred crystalline form II are shown in Table 22. The thermogravimetric-differential thermal analysis atlas TG-DTA of the polymorph II shows that there is an endothermic peak at 220° C., and an exothermic peak at 137° C.

The infra-red spectrogram of the crystalline form II shows that there are characteristic absorption peaks at 3431.13, 3056.96, 2979.82, 2931.60, 1643.24, 1633.59, 1583.45, 1504.37, 1434.94, 1415.65, 1340.43, 1305.72, 1213.14, 1155.28, 1114.78, 1064.63, 1041.49, 972.06, 862.12, 833.19, 773.40, 757.97, and 514.96 cm$^{-1}$.

Disclosed is also a revaprazan hydrochloride crystalline form III of the present invention, the melting point being 216-220° C.

In the powder X-ray diffraction pattern of the crystalline form III, 2θ, which is represented in degree with the characteristic diffraction peaks at 7.74±0.2, 24.42±0.2, 13.80±0.2, 7.38±0.2, and 25.62±0.2.

The powder X-ray diffraction peaks of further preferred crystalline form III are shown in Table 23. The thermogravimetric-differential thermal analysis atlas TG-DTA of the crystalline form III shows that there is an endothermic peak at 218° C. and an exothermic peak at 140° C.

The infra-red spectrogram of the crystalline form III shows that there are characteristic absorption peaks at 3421.48, 3265.26, 3043.46, 2979.82, 2931.60, 1643.24, 1633.59, 1583.45, 1504.37, 1434.94, 1413.72, 1340.43, 1303.79, 1218.93, 1155.28, 1114.78, 1064.63, 1039.56, 972.06, 862.12, 833.19, 773.40, 757.97, and 514.96 cm$^{-1}$.

Disclosed is also a revaprazan hydrochloride crystalline form IV of the present invention, the melting point being 215-219° C.

In the powder X-ray diffraction pattern of the crystalline form IV, 2θ, which is represented in degree with the characteristic diffraction peaks at 7.70±0.2, 10.34±0.2, 24.52±0.2, 20.04±0.2, and 13.78±0.2.

The powder X-ray diffraction peaks of further preferred crystalline form IV are shown in Table 24. The thermogravimetric-differential thermal analysis atlas TG-DTA of the polymorph IV shows that there is an endothermic peak at 217° C. and an exothermic peak at 130° C.

The infra-red spectrogram of the crystalline form IV shows that there are characteristic absorption peaks at 3473.56, 3407.98, 3269.12, 3060.82, 2981.74, 2933.53, 2896.88, 1643.24, 1633.59, 1585.38, 1504.37, 1433.01, 1415.65, 1340.43, 1305.72, 1211.21, 1157.21, 1112.85, 1062.70, 1043.42, 966.27, 833.19, 771.47, 757.97, and 518.82 cm$^{-1}$.

Disclosed is a revaprazan hydrochloride crystalline form V of the present invention, the melting point being 210-218° C.

In the powder X-ray diffraction pattern of the crystalline form V, 2θ, which is represented in degree with the characteristic diffraction peaks at 7.68±0.2, 24.52±0.2, 13.74±0.2, 8.06±0.2, and 19.54±0.2.

Powder X-ray diffraction peaks of further preferred crystalline form V are shown in Table 25.

The thermogravimetric-differential thermal analysis atlas TG-DTA of the crystalline form V shows that there is an endothermic peak at 216° C. and an exothermic peak at 143° C.

The infra-red spectrogram of the crystalline form V shows that there are characteristic absorption peaks at 3471.63, 3411.84, 3267.19, 3060.82, 2981.74, 2931.60, 2896.88, 1643.24, 1633.59, 1585.38, 1504.37, 1433.01, 1415.65, 1338.51, 1305.72, 1211.21, 1157.21, 1112.85, 1062.70, 1043.42, 966.27, 833.19, 771.47, 757.97 and 518.82 cm$^{-1}$.

A formulation containing revaprazan hydrochloride polymorphs of the present invention is composed of any one of the revaprazan hydrochloride crystalline forms I-V and pharmaceutically acceptable auxiliary materials.

In the formulation, the weight percentage of revaprazan hydrochloride polymorphs can be 0.1-99.9%, and the balanced is pharmaceutically acceptable carrier.

The formulation of the present invention is in a form of unit dosage, the unit dosage form refers to the unit of the formulation, such as a tablet for tablets, a capsule for capsules, a bottle for oral liquid, a sachet for granules and the like.

The form of the present invention can be any pharmaceutically acceptable dosage form, and the dosage forms include: tablets, sugar-coated tablets, film-coated tablets, enteric-coated tablets, capsules, hard capsules, soft capsules, oral liquid, buccal formulations, granules, electuaries, pills, powders, ointments, sublimed formulations, suspensions, pulvis, solutions, injections, suppositories, soft ointments, hard ointments, creams, sprays, drops and patches. Preferable oral dosage forms are present as follows: capsules, tablets, oral liquid, granules, pills, powders, sublimed formulations, ointments and the like.

The oral formulation of the present invention may include frequently-used excipients, such as binding agents, filling agents, diluting agents, tableting agents, lubricants, disintegrating agents, colorants, flavoring agents and wetting agents, and tablets can be coated if necessary.

Applicable filling agents include cellulose, mannitol, lactose and other similar filling agents. Suitable disintegrating agents include starch, polyvinylpyrrolidone and starch derivatives, such as sodium starch glycolate. The suitable lubricants include, for example magnesium stearate. Suitable pharmaceutically acceptable wetting agents include sodium dodecylsulfate, polyoxyethylene hydrogenated castor oil, Tween 80, polyoxyethylene 35 castor oil and sucrose fatty acid ester.

Solid oral compositions can be prepared by conventional methods such as blending, filling, tabletting and the like. By means of repeated blending, the active pharmaceutical ingredient (API) is distributed in those compositions where generally a large amount of filling agents are employed. The form of the oral liquid formulation can be, for example, aqueous or oily suspensions, solutions, emulsions, syrups or elixirs, or can be a dry product capable of being reconstituted with water or other suitable carriers before clinical use. The liquid formulation can contain conventional additives, such as suspending agents, for example sorbitol, syrup, methylcellulose, gelatine, hydroxyethyl cellulose, carboxymethyl cellulose, aluminum stearate gel or hydrogenated edible fat, and emulsifiers, for example lecithin, sorbitan monooleate or arabic gum; the non-aqueous carriers (which may comprises edible oil), such as almond oil and fractionated coconut oil, for example glyceride oily ester, propylene glycol or ethanol; and preservatives, such as paraben or propyl p-hydroxybenzoate or sorbic acid, and if necessary, conventional flavoring agents or colouring agents can be contained.

As for injections, the prepared liquid unit dosage form contains API and sterile carriers of the present invention. According to the carriers and concentrations, the compound can be suspended or dissolved. The solution is generally prepared by dissolving API in a carrier, filtering and sterilizing the carrier before being loaded into a suitable vial or an ampoule, and then sealing the vial or the ampoule. The auxiliary material, such as a local anesthetic, preservative and buffering agent, also can be dissolved in such carrier. In order to improve the stability, the composition is frozen after being loaded into the vial, and water is removed under vacuum.

A suitable pharmaceutically acceptable carrier is selectively added when preparing the medicament in the present invention, the pharmaceutically acceptable carrier is selected from: mannitol, sorbitol, sodium metabisulfite, sodium bisulfite, sodium thiosulfate, hydrochloric acid cysteine, mercaptoacetic acid, methionine, vitamin C, EDTA disodium, EDTA calcium disodium, monovalent alkali metal carbonate, acetate, phosphate or its aqueous solution, hydrochloric acid, acetic acid, sulfuric acid, phosphoric acid, amino acid, sodium chloride, potassium chloride, sodium lactate, xylitol, maltose, glucose, fructose, dextran, glycine, starch, sucrose, lactose, mannitol, silicon derivatives, cellulose and its derivatives, alginate, gelatin, polyethylene pyrrolidone, glycerin, Tween 80, agar, calcium carbonate, calcium bicarbonate, surfactant, polyethylene glycol, cyclodextrin, beta-cyclodextrin, phospholipids material, kaolin, talc, calcium stearate, magnesium stearate and the like.

When in use, usage and dosage are determined depending on the condition of the patient, 1-20 dosages may be taken every time and one to three times a day, such as: 1-20 sachets or pellets or tablets.

The preparation method of the revaprazan hydrochloride polymorph of the present invention, which is characterized by comprising the following steps:

(1) dissolving revaprazan hydrochloride with aqueous alcohol;

(2) adding active carbon, refluxing, decolorizing, filtering and the filtrate is obtained;

(3) cooling the filtrate, stirring, crystallizing, filtering, washing, obtaining solid, drying, and the polymorph is obtained.

The revaprazan hydrochloride is dissolved completely by adopting a mode of stirring, heating and dissolving in the above step (1). The heating and dissolving can also be carried out under the protection of argon or nitrogen, preferably the nitrogen.

The temperature reduction in the above step (2) can use ice-salt water bath or ice-water bath, preferably the ice-salt bath.

The aqueous alcohol in the above step (1) includes but not limited to ethanol, methanol, preferably the ethanol. The concentration of the aqueous alcohol is 45-98%.

88-98% of ethanol of the aqueous alcohol is further preferably used, and the polymorph obtained is polymorph I.

Specifically, placing the revaprazan hydrochloride in a reaction flask, adding 3-20 times (preferably 5-10 times of the amount, weight ratio, w/w) of 88-98% (preferably 90%)

ethanol aqueous solution, stirring and heating until it is dissolved completely, slightly cooling, adding active carbon, refluxing, and decolorizing for 5-15 minutes, filtering while hot and cooling to 0-15° C., stirring, crystallizing, filtering, and washing with 88-98% (preferably 90%) aqueous ethanol, filtering, drying, and polymorph I is obtained.

85% of ethanol of aqueous alcohol is further preferably used, and the polymorph obtained is crystalline form II.

Specifically: placing revaprazan hydrochloride in a reaction flask, adding 3-20 times (preferably 5-10 times of the amount, weight ratio, w/w) of 85% ethanol aqueous solution, stirring and heating until it is dissolved completely, slightly cooling, adding active carbon, refluxing and decolorizing for 5-15 minutes, filtering while hot and cooling to 0-15° C., stirring, crystallizing, filtering, washing and drying, and crystalline form II is obtained.

75% of ethanol of aqueous alcohol is further preferably used, and the polymorph obtained is crystalline form III.

Specifically: placing revaprazan hydrochloride in a reaction flask, adding 3-20 times (preferably 5-10 times of the amount, weight ratio, w/w) of 75% ethanol aqueous solution, stirring and heating until it is dissolved completely, slightly cooling, adding active carbon, refluxing and decolorizing for 5-15 minutes, filtering while hot and cooling to 0-15° C., stirring, crystallizing, filtering, washing and drying, and crystalline form III is obtained.

70% ethanol of aqueous alcohol is further preferably used, and the polymorph obtained is polymorph IV.

Specifically: placing revaprazan hydrochloride in a reaction flask, adding 3-20 times (preferably 5-10 times of the amount, weight ratio, w/w) of 70% ethanol aqueous solution, stirring and heating until it is dissolved completely, slightly cooling, adding active carbon, refluxing, and decolorizing for 5-15 minutes, filtering while hot and cooling to 0-15° C., stirring, crystallizing, filtering, washing and drying, and crystalline form IV is obtained.

50% ethanol of aqueous alcohol is further preferably used, and the polymorph obtained is crystalline form V.

Specifically: placing revaprazan hydrochloride in a reaction flask, adding 3-20 times (preferably 5-10 times of the amount, weight ratio, w/w) of 50% ethanol aqueous solution, stirring and heating until it is dissolved completely, slightly cooling, adding active carbon and refluxing, decolorizing for 5-15 minutes, filtering while hot and cooling to 0-15° C., stirring and crystallizing, filtering, washing and drying, and crystalline form V is obtained.

Beneficial Effects

In order to better illustrate beneficial effects of the revaprazan hydrochloride polymorphs of the present invention, the following describes beneficial effects by using stability tests.

Testing Examples: Stability

1. Stability of Revaprazan Hydrochloride Crystal Form I

Revaprazan Hydrochloride Crystalline Form I (Embodiment 1)

1.1 Light Illumination Test

Revaprazan hydrochloride crystalline form I is irradiated under such a condition that the light intensity is 4500±500 Lx, and is sampled on the $5^{th}$ day and $10^{th}$ day for detection, and the results are shown in Table 1.

TABLE 1

Results of intense light illumination test of revaprazan hydrochloride crystalline form I

| Time (Days) | Appearance color | Loss on drying (%) | Purity (%) | Relevant substances |
|---|---|---|---|---|
| Day 0 | White powder | 0.27 | 99.96 | Not detected |
| $5^{th}$ day | White powder | 0.28 | 99.92 | Not detected |
| $10^{th}$ day | White powder | 0.30 | 99.94 | Not detected |

1.2 High Temperature Test

Revaprazan hydrochloride crystalline form I is placed in a 60° C. incubator, and is sampled on the $5^{th}$ day and $10^{th}$ day for detection, and the results are shown in Table 2.

TABLE 2

Results of high temperature test of revaprazan hydrochloride crystalline form I

| Time (Days) | Appearance color | Loss on drying (%) | Purity (%) | Relevant substances |
|---|---|---|---|---|
| Day 0 | White powder | 0.21 | 99.96 | Not detected |
| $5^{th}$ day | White powder | 0.23 | 99.95 | Not detected |
| $10^{th}$ day | White powder | 0.24 | 99.98 | Not detected |

1.3 High Humidity Test

Revaprazan hydrochloride crystalline form I is placed in an incubator of 25° C. (relative humidity of 75±5%), and is sampled on the $5^{th}$ day and $10^{th}$ day for detection. The results are shown in Table 3.

TABLE 3

Results of high humidity test of revaprazan hydrochloride crystalline form I

| Time (Days) | Appearance color | Weight gain upon moisture absorption (%) | Purity (%) | Relevant substances |
|---|---|---|---|---|
| Day 0 | White powder | 0 | 99.96 | Not detected |
| $5^{th}$ day | White powder | 0.42 | 99.93 | Not detected |
| $10^{th}$ day | White powder | 0.63 | 99.95 | Not detected |

1.4 Accelerated Test

Revaprazan hydrochloride crystalline form I is sealed in a polyethylene film bag, is placed for 6 months under the conditions that the temperature is 40±2° C. and the relative humidity is 75±5%, and is respectively sampled at the end of the $1^{st}$ Month, the $2^{nd}$ Month, the $3^{rd}$ Month and the $6^{th}$ Month for detection; and the results are shown in Table 4.

TABLE 4

Results of accelerated test of revaprazan hydrochloride crystalline form I

| Test time | Appearance color | Purity (%) | Relevant substances |
|---|---|---|---|
| Month 0 | White powder | 99.96 | Not detected |
| $1^{st}$ month | White powder | 99.97 | Not detected |
| $2^{nd}$ month | White powder | 99.92 | Not detected |
| $3^{rd}$ month | White powder | 99.96 | Not detected |
| $6^{th}$ month | White powder | 99.95 | Not detected |

The results indicate that: revaprazan hydrochloride crystalline form I is stable under the conditions of intense light illumination, high temperature, high humidity and accelerated tests, without obvious changes in appearance color, loss on drying, purity and relevant substances, and has a slight weight gain upon moisture absorption under the condition of high humidity.

2. Stability of Revaprazan Hydrochloride Crystalline Form II

Revaprazan Hydrochloride Crystalline Form II (Embodiment 2)

2.1 Light Illumination Test

Revaprazan hydrochloride crystalline form II is irradiated under the condition that the light intensity is 4500±500Lx, and is sampled on the $5^{th}$ day and $10^{th}$ day for detection. The results are shown in Table 5.

TABLE 5

Results of intense light illumination test of revaprazan hydrochloride crystalline form II

| Time (Days) | Appearance color | Loss on drying (%) | Purity (%) | Relevant substances |
|---|---|---|---|---|
| Day 0 | White powder | 0.25 | 99.94 | Not detected |
| $5^{th}$ day | White powder | 0.26 | 99.97 | Not detected |
| $10^{th}$ day | White powder | 0.28 | 99.94 | Not detected |

2.2 High Temperature Test

Revaprazan hydrochloride crystalline form II is placed in a 60° C. incubator, and is sampled on the $5^{th}$ day and $10^{th}$ day for detection, and the results are shown in Table 6.

TABLE 6

Results of high temperature test of revaprazan hydrochloride crystalline form II

| Time (Days) | Appearance color | Loss on drying (%) | Purity (%) | Relevant substances |
|---|---|---|---|---|
| Day 0 | White powder | 0.23 | 99.94 | Not detected |
| $5^{th}$ day | White powder | 0.27 | 99.97 | Not detected |
| $10^{th}$ day | White powder | 0.29 | 99.95 | Not detected |

2.3 High Humidity Test

Revaprazan hydrochloride crystalline form II is placed in an incubator of 25° C. (relative humidity of 75±5%), and is sampled on the $5^{th}$ day and $10^{th}$ day for detection. The results are shown in Table 7.

TABLE 7

Results of high humidity test of revaprazan hydrochloride crystalline form II

| Time (Days) | Appearance color | Weight gain upon moisture absorption (%) | Purity (%) | Relevant substances |
|---|---|---|---|---|
| Day 0 | White powder | 0 | 99.94 | Not detected |
| $5^{th}$ day | White powder | 0.42 | 99.93 | Not detected |
| $10^{th}$ day | White powder | 0.64 | 99.95 | Not detected |

2.4 Accelerated Test

Revaprazan hydrochloride crystalline form II is sealed in a polyethylene film bag and is placed for 6 months under the conditions that the temperature is 40±2° C. and the relative humidity is 75±5%, and is respectively sampled at the end of the $1^{st}$ Month, the $2^{nd}$ Month, the $3^{rd}$ Month and the $6^{th}$ Month for detection; and the results are shown in Table 8.

TABLE 8

Results of accelerated test of revaprazan hydrochloride crystalline form II

| Test time | Appearance color | Purity (%) | Relevant substances |
|---|---|---|---|
| Month 0 | White powder | 99.94 | White powder |
| $1^{st}$ month | White powder | 99.93 | White powder |
| $2^{nd}$ month | White powder | 99.95 | White powder |
| $3^{rd}$ month | White powder | 99.96 | White powder |
| $6^{th}$ month | White powder | 99.95 | White powder |

The results indicate that: revaprazan hydrochloride crystalline form II is stable under the conditions of intensive light illumination, high temperature, high humidity and accelerated test, without obvious changes in appearance color, loss on drying, purity and relevant substance, and has slight weight gain upon moisture absorption under high humidity condition.

3. Stability of Revaprazan Hydrochloride Crystalline Form III

Revaprazan Hydrochloride Polymorph III (Embodiment 3)

3.1 Light Illumination Test

Revaprazan hydrochloride polymorph III is irradiated under such a condition that the light intensity is 4500±500Lx, and is sampled on the $5^{th}$ day and $10^{th}$ day for detection. The results are shown in Table 9.

TABLE 9

Results of intensive light illumination test of revaprazan hydrochloride polymorph III

| Time (Day) | Appearance color | Loss on drying (%) | Purity (%) | Relevant substances |
|---|---|---|---|---|
| Day 0 | White powder | 0.28 | 99.95 | Undetected |
| $5^{th}$ day | White powder | 0.25 | 99.92 | Undetected |
| $10^{th}$ day | White powder | 0.29 | 99.95 | Undetected |

3.2 High-Temperature Test

Revaprazan hydrochloride polymorph III is placed in an incubator of 60° C., and is sampled on the $5^{th}$ day and the $10^{th}$ day for detection. The results are shown in Table 10.

TABLE 10

Stability results of high-temperature test of revaprazan hydrochloride polymorph III

| Time (Day) | Appearance color | Loss on drying (%) | Purity (%) | Relevant substances |
|---|---|---|---|---|
| Day 0 | White powder | 0.22 | 99.95 | Undetected |
| $5^{th}$ day | White powder | 0.26 | 99.94 | Undetected |
| $10^{th}$ day | White powder | 0.26 | 99.92 | Undetected |

3.3 High-Humidity Test

Revaprazan hydrochloride polymorph III is placed in an incubator of 25° C. (relative humidity of 75±5%), and is sampled on the $5^{th}$ day and the $10^{th}$ day for detection. The results are shown in Table 11.

TABLE 11

Stability results of high humidity test of revaprazan hydrochloride crystalline form III

| Time (Day) | Appearance color | Weight gain upon moisture absorption (%) | Purity (%) | Relevant substances |
|---|---|---|---|---|
| Day 0 | White powder | 0 | 99.95 | Undetected |
| 5$^{th}$ day | White powder | 0.47 | 99.92 | Undetected |
| 10$^{th}$ day | White powder | 0.59 | 99.94 | Undetected |

3.4 Accelerated Test

Revaprazan hydrochloride crystalline form III is sealed in a polyethylene film bag, is placed for 6 months under the conditions that the temperature is 40±2° C. and the relative humidity is 75±5%, and is sampled at the end of the 1$^{st}$ Month, the 2$^{nd}$ Month, the 3$^{rd}$ Month and the 6$^{th}$ Month for detection. The results are shown in Table 12.

TABLE 12

Results of accelerated test of revaprazan hydrochloride crystalline form III

| Test time | Appearance color | Purity (%) | Relevant substances |
|---|---|---|---|
| Month 0 | White powder | 99.95 | Undetected |
| 1$^{st}$ month | White powder | 99.92 | Undetected |
| 2$^{nd}$ month | White powder | 99.91 | Undetected |
| 3$^{rd}$ month | White powder | 99.93 | Undetected |
| 6$^{th}$ month | White powder | 99.95 | Undetected |

The results indicate that: revaprazan hydrochloride crystalline form III is stable under the conditions of intensive light illumination, high temperature, high humidity and accelerated test, without obvious changes in appearance color, loss on drying, purity and relevant substance, and has slight weight gain upon moisture absorption under high humidity condition.

4. Stability of Revaprazan Hydrochloride Crystalline Form IV

Revaprazan Hydrochloride Crystalline Form IV
(Test Example 4)

4.1 Light Illumination Test

Revaprazan hydrochloride crystalline form III is irradiated under such a condition that the light intensity is 4500±500Lx, and is sampled on the 5$^{th}$ day and the 10$^{th}$ day for detection. The results are shown in Table 13.

TABLE 13

Results of intensive light illumination test of revaprazan hydrochloride crystalline form IV

| Time (Day) | Appearance color | Loss on drying (%) | Purity (%) | Relevant substances |
|---|---|---|---|---|
| Day 0 | White powder | 0.27 | 99.93 | Undetected |
| 5$^{th}$ day | White powder | 0.29 | 99.95 | Undetected |
| 10$^{th}$ day | White powder | 0.31 | 99.92 | Undetected |

4.2 High-Temperature Test

Revaprazan hydrochloride crystalline form IV is placed in an incubator of 60° C., and is sampled on the 5$^{th}$ day and the 10$^{th}$ day for detection. The results are shown in Table 14.

TABLE 14

Stability results of high-temperature test of revaprazan hydrochloride crystalline form IV

| Time (Day) | Appearance color | Loss on drying (%) | Purity (%) | Relevant substances |
|---|---|---|---|---|
| Day 0 | White powder | 0.25 | 99.93 | Undetected |
| 5$^{th}$ day | White powder | 0.27 | 99.91 | Undetected |
| 10$^{th}$ day | White powder | 0.27 | 99.92 | Undetected |

4.3 High-Humidity Test

Revaprazan hydrochloride crystalline form IV is placed in an incubator of 25° C. (relative humidity of 75±5%), and is sampled on the 5$^{th}$ day and the 10$^{th}$ day for detection The results are shown in Table 15.

TABLE 15

Stability results of high-humidity test of revaprazan hydrochloride crystalline form IV

| Time (Day) | Appearance color | Weight gain upon moisture absorption (%) | Purity (%) | Relevant substances |
|---|---|---|---|---|
| Day 0 | White powder | 0 | 99.93 | White powder |
| 5$^{th}$ day | White powder | 0.44 | 99.96 | White powder |
| 10$^{th}$ day | White powder | 0.62 | 99.93 | White powder |

4.4 Accelerated Test

Revaprazan hydrochloride crystalline form IV is sealed in a polyethylene film bag, is placed for 6 months under the conditions that the temperature is 40±2° C. and the relative humidity is 75±5%, and is sampled at the end of the 1$^{st}$ Month, the 2$^{nd}$ Month, the 3$^{rd}$ Month and the 6$^{th}$ Month for detection. The results are shown in Table 16.

TABLE 16

Results of accelerated test of revaprazan hydrochloride crystalline form IV

| Test time | Appearance color | Purity (%) | Relevant substances |
|---|---|---|---|
| Month 0 | White powder | 99.93 | Undetected |
| 1$^{st}$ month | White powder | 99.91 | Undetected |
| 2$^{nd}$ month | White powder | 99.90 | Undetected |
| 3$^{rd}$ month | White powder | 99.95 | Undetected |
| 6$^{th}$ month | White powder | 99.94 | Undetected |

The results indicate that: revaprazan hydrochloride crystalline form IV is stable under the conditions of intense light illumination, high temperature, high humidity and acceleration tests, without obvious changes in appearance colour, loss on drying, impurity and related substances, and has a slight weight gain upon moisture absorption.

5. Stability of Revaprazan Hydrochloride Crystalline Form V

Revaprazan Hydrochloride Crystalline Form V
(Test Example 5)

5.1 Light Illumination Test

Revaprazan hydrochloride crystalline form V is irradiated under the light intensity condition of 4500±500Lx; and is sampled on the 5$^{th}$ day and 10$^{th}$ day for detection. The results are shown in Table 17.

TABLE 17

Results of intense light illumination test
of revaprazan hydrochloride crystalline form

| Time (Days) | Appearance color | Loss on drying (%) | Purity (%) | Related substances |
|---|---|---|---|---|
| Day 0 | White powder | 0.24 | 99.94 | Undetected |
| 5$^{th}$ Day | White powder | 0.27 | 99.95 | Undetected |
| 10$^{th}$ Day | White powder | 0.30 | 99.95 | Undetected |

5.2 High Temperature Test

Revaprazan hydrochloride crystal form 4 is placed in an incubator of 60° C.; and is sampled on the 5$^{th}$ day and the 10$^{th}$ day for detection, and the results are shown in Table 23.

TABLE 18

Results of stability of high temperature test
of revaprazan hydrochloride crystalline form V

| Time (Days) | Appearance color | Loss on drying (%) | Purity (%) | Related substances |
|---|---|---|---|---|
| Day 0 | White powder | 0.29 | 99.94 | Undetected |
| 5$^{th}$ Day | White powder | 0.30 | 99.95 | Undetected |
| 10$^{th}$ Day | White powder | 0.32 | 99.92 | Undetected |

5.3 High Humidity Test

Revaprazan hydrochloride crystal form 4 is placed in an incubator of 25° C. (the relative humidity is 75±5%), and is sampled on the 5$^{th}$ day and the 10$^{th}$ day for detection. The results are shown in Table 19.

TABLE 19

Results of stability of high humidity test
of revaprazan hydrochloride crystalline form V

| Time (Days) | Appearance color | Weight gain upon moisture absorption (%) | Purity (%) | Related substances |
|---|---|---|---|---|
| Day 0 | White powder | 0 | 99.94 | White powder |
| 5$^{th}$ Day | White powder | 0.42 | 99.94 | White powder |
| 10$^{th}$ Day | White powder | 0.66 | 99.96 | White powder |

5.4 Acceleration Test

Revaprazan hydrochloride crystalline form V is sealed in a polyethylene film bag and is placed for 6 months under the condition that the temperature is 40±2° C. and the relative humidity is 75±5%, and is sampled at the end of the 1$^{st}$ month, the 2$^{nd}$ month, the 3$^{rd}$ month and the 6$^{th}$ month for detection, and the results are shown in Table 20.

TABLE 20

Results of acceleration test of revaprazan hydrochloride crystalline form V

| Test time | Appearance color | Purity (%) | Related substances |
|---|---|---|---|
| Month 0 | White powder | 99.94 | Undetected |
| 1$^{st}$ Month | White powder | 99.98 | Undetected |
| 2$^{nd}$ Month | White powder | 99.95 | Undetected |
| 3$^{rd}$ Month | White powder | 99.97 | Undetected |
| 6$^{th}$ Month | White powder | 99.94 | Undetected |

The results indicate that: revaprazan hydrochloride crystalline form V is stable under the conditions of intense light illumination, high temperature, high humidity and accelerated tests, without obvious changes in appearance color, loss on drying, purity and relevant substances, and has a slight weight gain upon moisture absorption under the condition of high humidity.

The five crystal forms of revaprazan hydrochloride prepared by using the method of the present invention have high product purities which are more than 99.9%; moreover, they have high yields which are about 90%. Besides, the five crystal forms are stable during light illumination, high temperature, high humidity and acceleration tests, and their impurities show no significant changes.

DETAILED DESCRIPTION OF EMBODIMENTS

The present invention is further described below in detail through embodiments, but it is not intended to further define the present invention.

PRODUCT EMBODIMENTS

Embodiment 1 Revaprazan Hydrochloride Crystalline Form I

Figure 1:
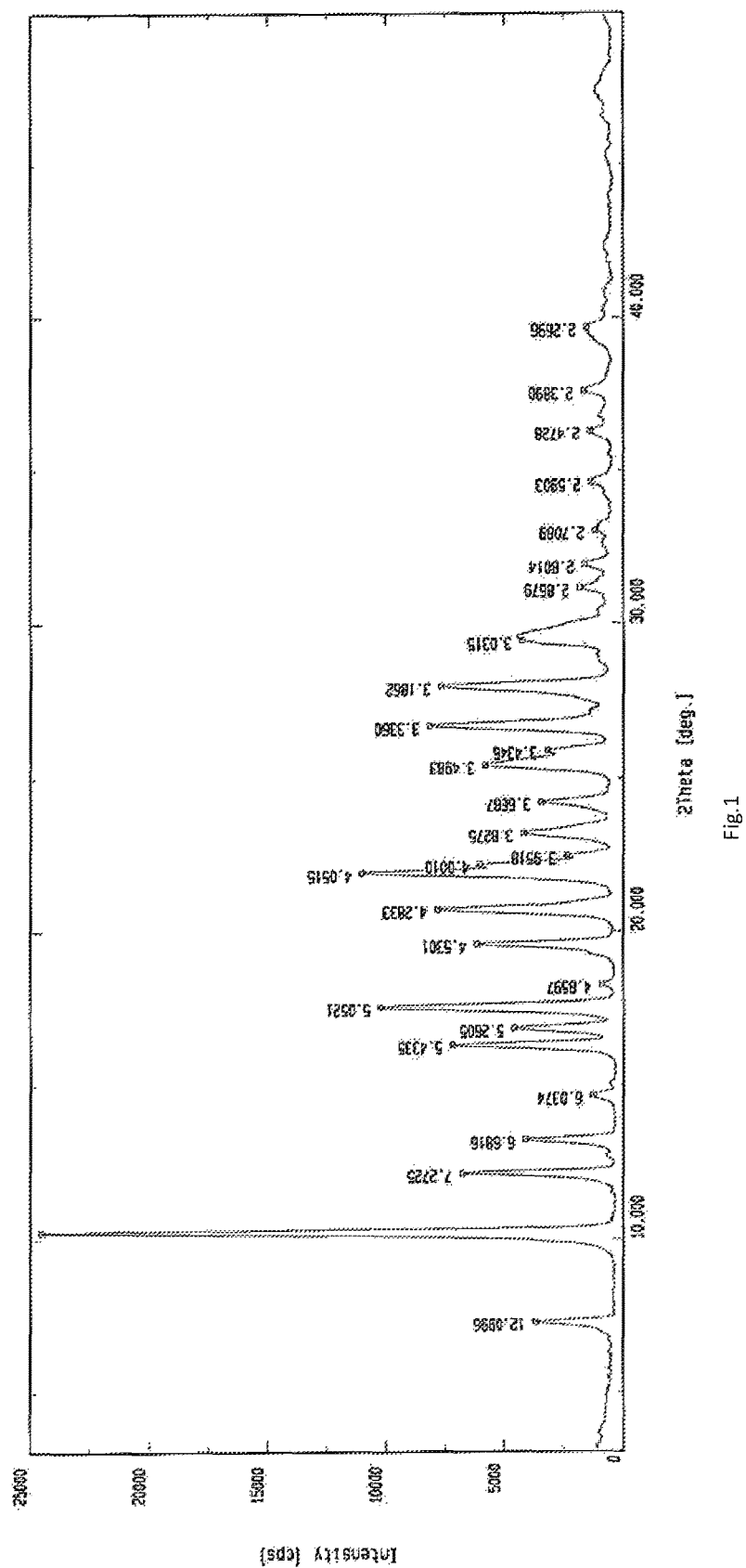
FIG. 1 Powder X-ray diffraction pattern of crystal form I
FIG. 2 TG-DTA diagram of crystal form I
FIG. 3 Infra-red spectrogram of crystal form I
FIG. 4 Powder X-ray diffraction pattern of crystal form II
FIG. 5 TG-DTA diagram of crystal form II
FIG. 6 Infra-red spectrogram of crystal form II
FIG. 7 Powder X-ray diffraction pattern of crystal form III
FIG. 8 TG-DTA diagram of crystal form III
FIG. 9 Infra-red spectrogram of crystal form III
FIG. 10 Powder X-ray diffraction pattern of crystal form IV
FIG. 11 TG-DTA diagram of crystal form IV
FIG. 12 Infra-red spectrogram of crystal form IV
FIG. 13 Powder X-ray diffraction pattern of crystal form V
FIG. 14 TG-DTA diagram of crystal form V
FIG. 15 Infra-red spectrogram of crystal form V

For revaprazan hydrochloride crystalline form I, in its powder X-ray diffraction pattern, 2θ, which is represented in degree, the characteristic diffraction peaks at 10.24±0.2, 21.92±0.2, 17.54±0.2, 26.70±0.2 and 20.72±0.2. Its powder X-ray diffraction data is shown in Table 21, and its powder X-ray diffraction pattern is shown in FIG. 1.

TABLE 21

Parameters of characteristic peaks of powder X-ray diffraction pattern
of revaprazan hydrochloride crystalline form I

| Number | 2θ | d value | Relative intensity I/I$^0$ |
|---|---|---|---|
| 1 | 7.300 | 12.0996 | 15 |
| 2 | 10.240 | 8.6314 | 100 |
| 3 | 12.160 | 7.2725 | 28 |
| 4 | 13.240 | 6.6816 | 17 |
| 5 | 14.660 | 6.0374 | 5 |
| 6 | 16.300 | 5.4335 | 29 |
| 7 | 16.840 | 5.2605 | 19 |
| 8 | 17.540 | 5.0521 | 42 |
| 9 | 18.240 | 4.8597 | 4 |
| 10 | 19.580 | 4.5301 | 25 |
| 11 | 20.720 | 4.2833 | 32 |
| 12 | 21.920 | 4.0515 | 45 |
| 13 | 22.200 | 4.0010 | 25 |

TABLE 21-continued

Parameters of characteristic peaks of powder X-ray diffraction pattern of revaprazan hydrochloride crystalline form I

| Number | 2θ | d value | Relative intensity I/I° |
|---|---|---|---|
| 14 | 22.480 | 3.9518 | 10 |
| 15 | 23.220 | 3.8275 | 17 |
| 16 | 24.240 | 3.6687 | 14 |
| 17 | 25.440 | 3.4983 | 24 |
| 18 | 25.920 | 3.4346 | 13 |
| 19 | 26.700 | 3.3360 | 33 |
| 20 | 27.980 | 3.1862 | 31 |
| 21 | 29.440 | 3.0315 | 17 |
| 22 | 31.160 | 2.8679 | 7 |
| 23 | 31.920 | 2.8014 | 7 |
| 24 | 33.040 | 2.7089 | 5 |
| 25 | 34.600 | 2.5903 | 6 |
| 26 | 36.300 | 2.4728 | 6 |
| 27 | 37.620 | 2.3890 | 7 |
| 28 | 39.680 | 2.2696 | 6 |

Figure 2:
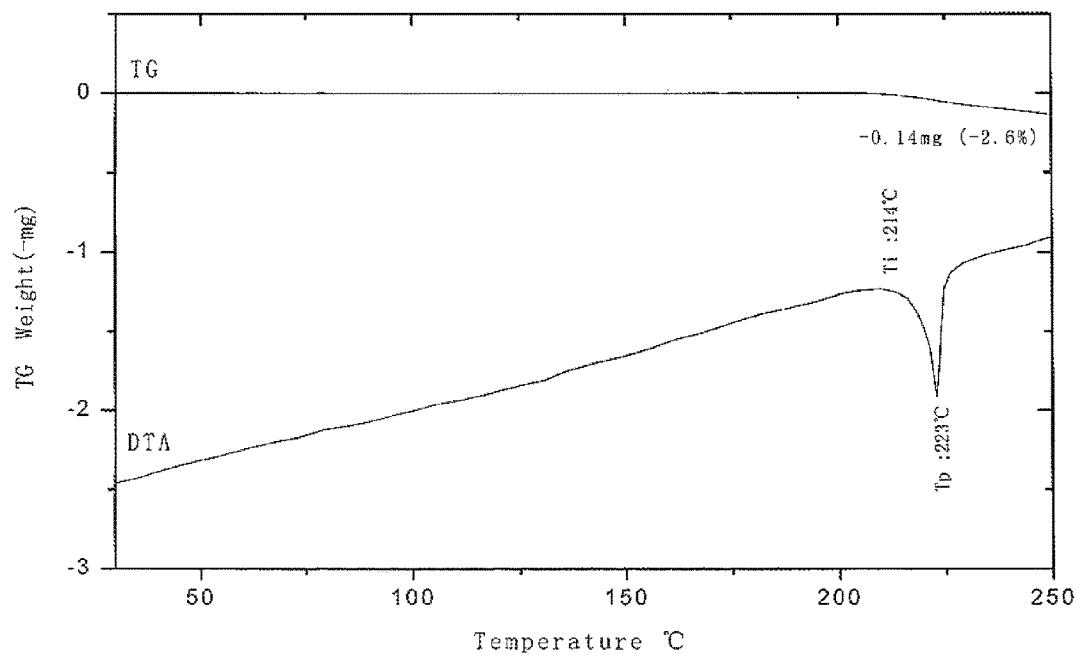
Figure 3:
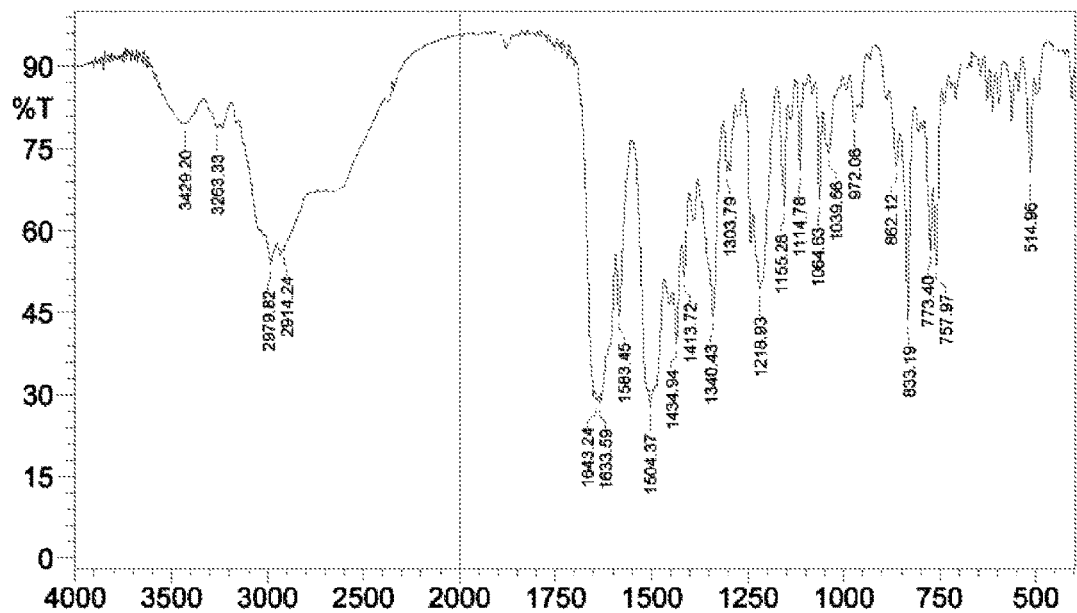

The thermogravimetry-differential thermal analysis atlas (TG-DTA) shows that crystalline form I has endothermic peaks at the temperature of 223° C., which is shown in FIG. 2. The infra-red spectrogram of crystalline form I shows that there are characteristic absorption peaks at 3429.20, 3263.33, 2979.82, 2914.24, 1643.24, 1633.59, 1583.45, 1504.37, 1434.94, 1413.72, 1340.43, 1303.79, 1218.93, 1155.28, 1114.78, 1064.63, 1039.56, 972.06, 862.12, 833.19, 773.40, 757.97 and 514.96. Its infra-red spectrogram is shown in FIG. 3.

Embodiment 2 Revaprazan Hydrochloride Crystalline Form II

Figure 4:
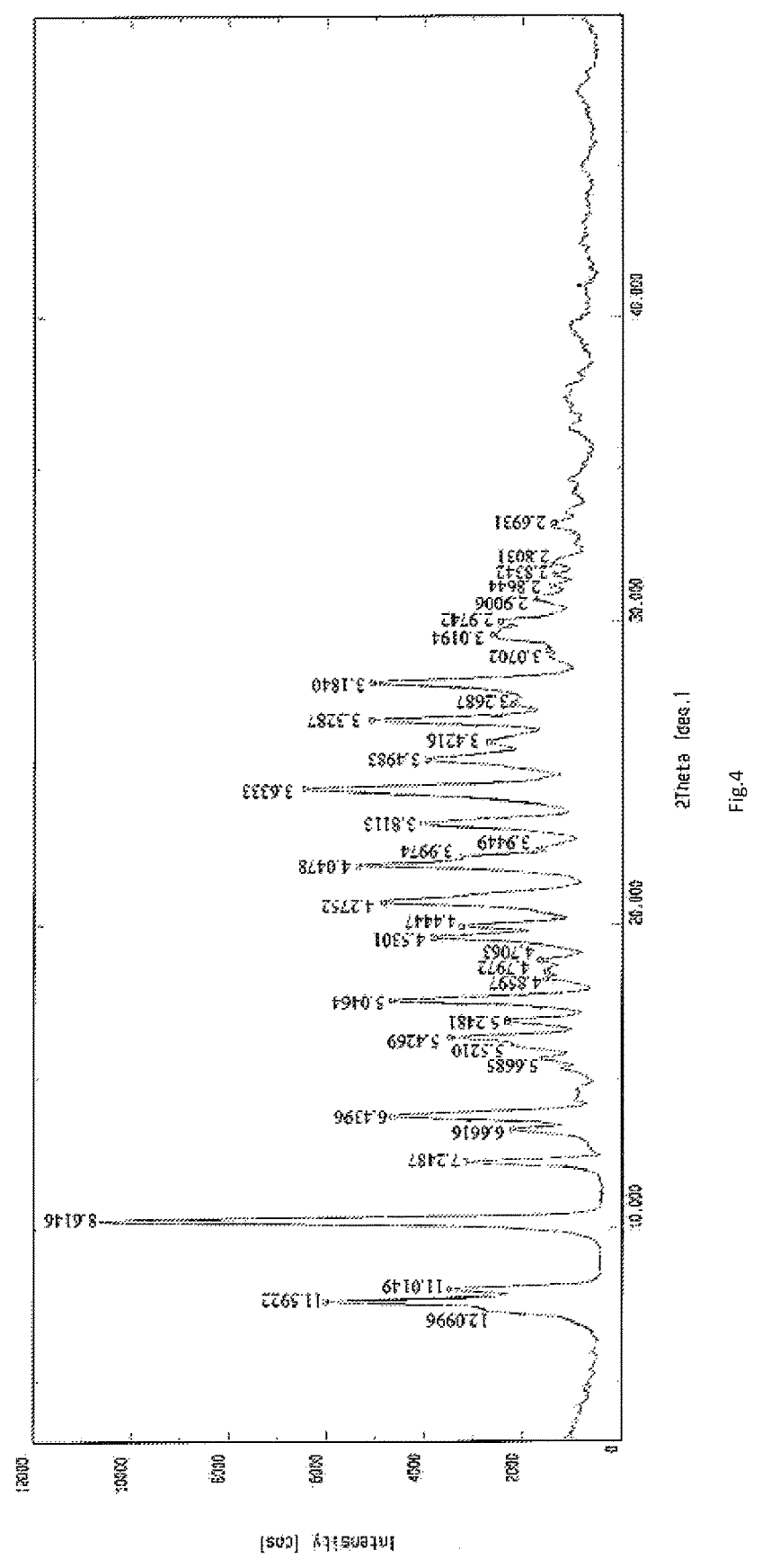

In the powder X-ray diffraction pattern of revaprazan hydrochloride crystalline form II, 2θ which is represented in degree, the characteristic diffraction peaks at 10.26±0.2, 24.48±0.2, 7.62±0.2, 21.94±0.2, 26.76±0.2 and 28.00±0.2. The specific powder X-ray diffraction data is shown in Table 22, and its powder X-ray diffraction pattern is shown in FIG. 4.

TABLE 22

Parameters of characteristic peaks of powder X-ray diffraction pattern of revaprazan hydrochloride crystalline form II

| Serial Number | 2θ | d value | Relative intensity I/I° |
|---|---|---|---|
| 1 | 7.300 | 12.0996 | 25 |
| 2 | 7.620 | 11.5922 | 55 |
| 3 | 8.020 | 11.0149 | 32 |
| 4 | 10.260 | 8.6146 | 100 |
| 5 | 12.200 | 7.2487 | 29 |
| 6 | 13.280 | 6.6616 | 20 |
| 7 | 13.740 | 6.4396 | 42 |
| 8 | 15.620 | 5.6685 | 15 |
| 9 | 16.040 | 5.5210 | 20 |
| 10 | 16.320 | 5.4269 | 32 |
| 11 | 16.880 | 5.2481 | 21 |
| 12 | 17.560 | 5.0464 | 42 |
| 13 | 18.240 | 4.8597 | 14 |
| 14 | 18.480 | 4.7972 | 14 |
| 15 | 18.840 | 4.7063 | 15 |
| 16 | 19.580 | 4.5301 | 35 |
| 17 | 19.960 | 4.4447 | 30 |
| 18 | 20.760 | 4.2752 | 44 |
| 19 | 21.940 | 4.0478 | 49 |
| 20 | 22.220 | 3.9974 | 30 |
| 21 | 22.520 | 3.9449 | 15 |

TABLE 22-continued

Parameters of characteristic peaks of powder X-ray diffraction pattern of revaprazan hydrochloride crystalline form II

| Serial Number | 2θ | d value | Relative intensity I/I° |
|---|---|---|---|
| 22 | 23.320 | 3.8113 | 37 |
| 23 | 24.480 | 3.6333 | 58 |
| 24 | 25.440 | 3.4983 | 36 |
| 25 | 26.020 | 3.4216 | 24 |
| 26 | 26.760 | 3.3287 | 46 |
| 27 | 27.260 | 3.2687 | 20 |
| 28 | 28.000 | 3.1840 | 46 |
| 29 | 29.060 | 3.0702 | 14 |
| 30 | 29.560 | 3.0194 | 24 |
| 31 | 30.020 | 2.9742 | 22 |
| 32 | 30.800 | 2.9006 | 16 |
| 33 | 31.200 | 2.8644 | 13 |
| 34 | 31.540 | 2.8342 | 12 |
| 35 | 31.900 | 2.8031 | 13 |
| 36 | 33.240 | 2.6931 | 12 |

Figure 5:
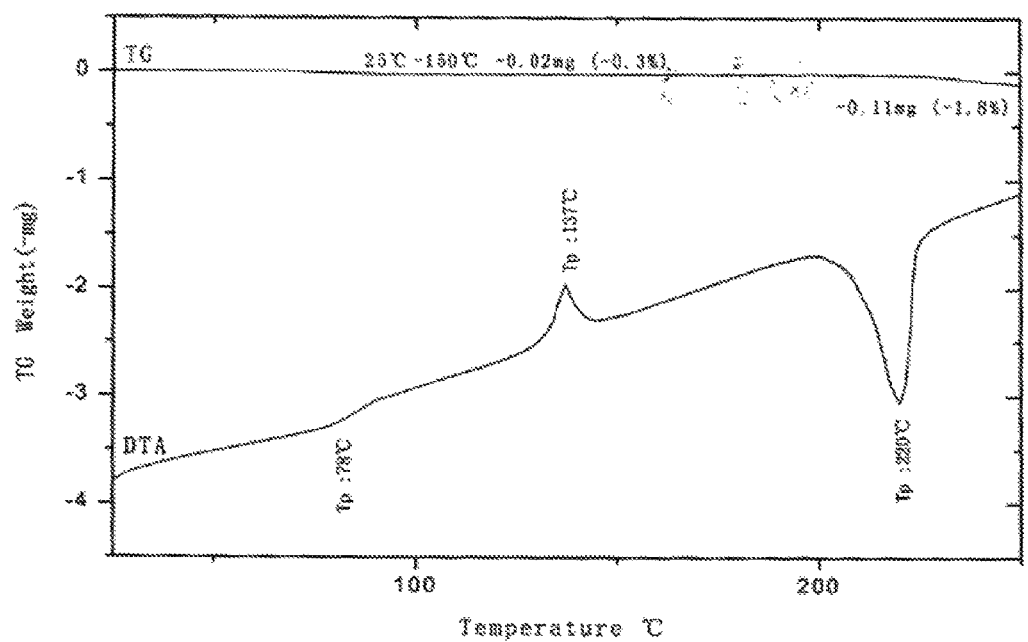
Figure 6:
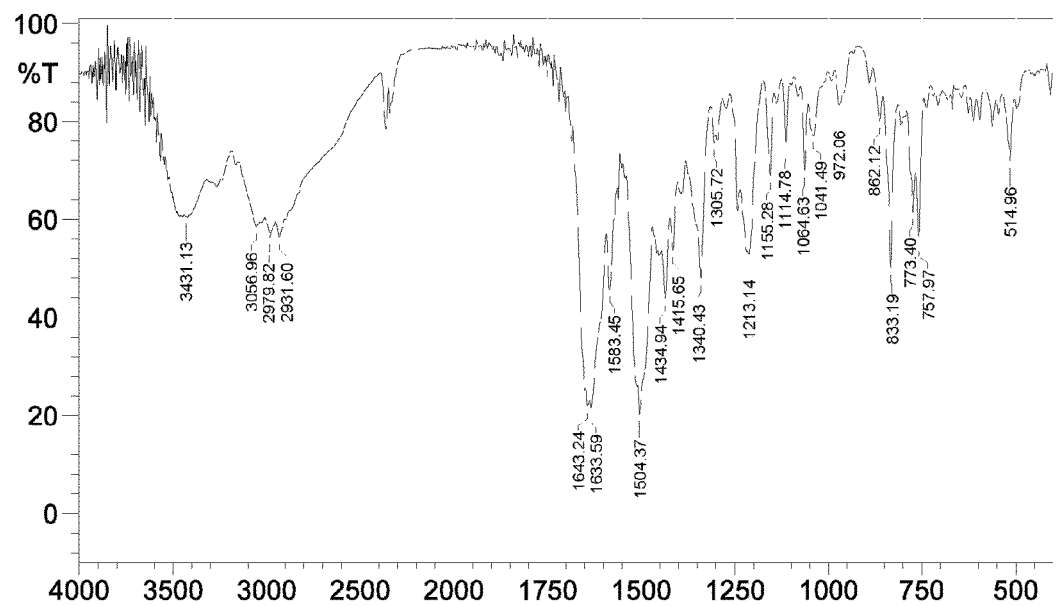

The thermogravimetry-differential thermal analysis atlas (TG-DTA) shows that crystalline form II has an endothermic peak at 220° C., and has an exothermic peak at 137° C., which are shown in FIG. 5. The infra-red spectrogram of crystalline form II shows that it has characteristic absorption peaks at 3431.13, 3056.96, 2979.82, 2931.60, 1643.24, 1633.59, 1583.45, 1504.37, 1434.94, 1415.65, 1340.43, 1305.72, 1213.14, 1155.28, 1114.78, 1064.63, 1041.49, 972.06, 862.12, 833.19, 773.40, 757.97 and 514.96 cm$^{-1}$. The infra-red spectrogram is shown in FIG. 6.

Embodiment 3 Revaprazan Hydrochloride Crystalline Form III

Figure 7:
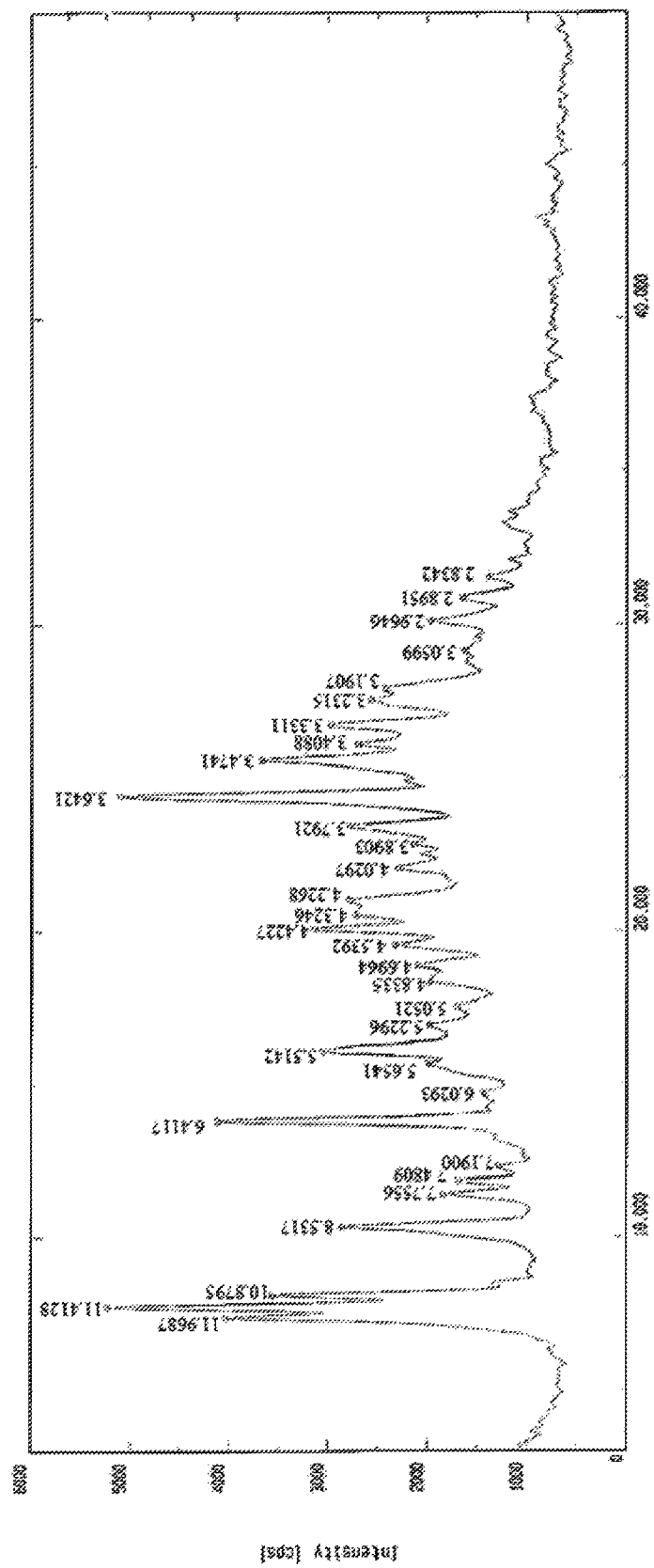

In the powder X-ray diffraction pattern of revaprazan hydrochloride crystalline form III, 2θ, which is represented in degree, the characteristic diffraction peaks at 7.74±0.2, 24.42±0.2, 13.80±0.2, 7.38±0.2 and 25.62±0.2. The specific powder X-ray diffraction data is shown in Table 23, and its powder X-ray diffraction pattern is shown in FIG. 7.

TABLE 23

Parameters of characteristic peaks of powder X-ray diffraction pattern of revaprazan hydrochloride crystalline form III

| Serial Number | 2θ | d value | Relative intensity I/I° |
|---|---|---|---|
| 1 | 7.380 | 11.9687 | 77 |
| 2 | 7.740 | 11.4128 | 100 |
| 3 | 8.120 | 10.8795 | 68 |
| 4 | 10.360 | 8.5317 | 55 |
| 5 | 11.400 | 7.7556 | 35 |
| 6 | 11.820 | 7.4809 | 32 |
| 7 | 12.300 | 7.1900 | 24 |
| 8 | 13.800 | 6.4117 | 79 |
| 9 | 14.680 | 6.0293 | 28 |
| 10 | 15.660 | 5.6541 | 38 |
| 11 | 16.060 | 5.5142 | 59 |
| 12 | 16.940 | 5.2296 | 38 |
| 13 | 17.540 | 5.0521 | 33 |
| 14 | 18.340 | 4.8335 | 38 |
| 15 | 18.880 | 4.6964 | 40 |
| 16 | 19.540 | 4.5392 | 45 |
| 17 | 20.060 | 4.4227 | 60 |
| 18 | 20.520 | 4.3246 | 52 |
| 19 | 21.000 | 4.2268 | 53 |
| 20 | 22.040 | 4.0297 | 44 |
| 21 | 22.840 | 3.8903 | 41 |
| 22 | 23.440 | 3.7921 | 53 |
| 23 | 24.420 | 3.6421 | 98 |

TABLE 23-continued

Parameters of characteristic peaks of powder X-ray diffraction pattern of revaprazan hydrochloride crystalline form III

| Serial Number | 2θ | d value | Relative intensity I/I⁰ |
|---|---|---|---|
| 24 | 25.620 | 3.4741 | 70 |
| 25 | 26.120 | 3.4088 | 52 |
| 26 | 26.740 | 3.3311 | 57 |
| 27 | 27.580 | 3.2315 | 49 |
| 28 | 27.940 | 3.1907 | 47 |
| 29 | 29.160 | 3.0599 | 31 |
| 30 | 30.120 | 2.9646 | 38 |
| 31 | 30.860 | 2.8951 | 32 |
| 32 | 31.540 | 2.8342 | 27 |

Figure 8:
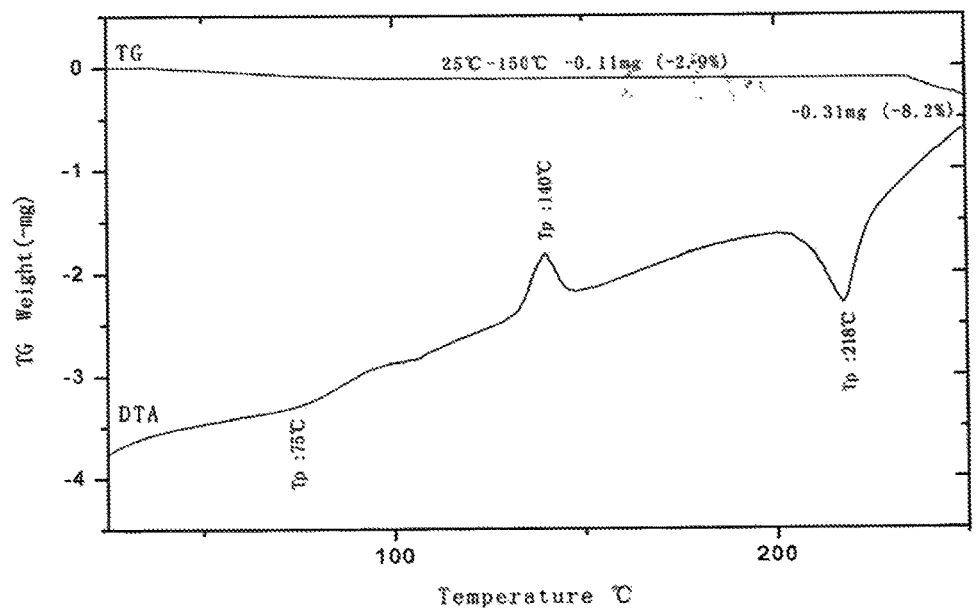
Figure 9:
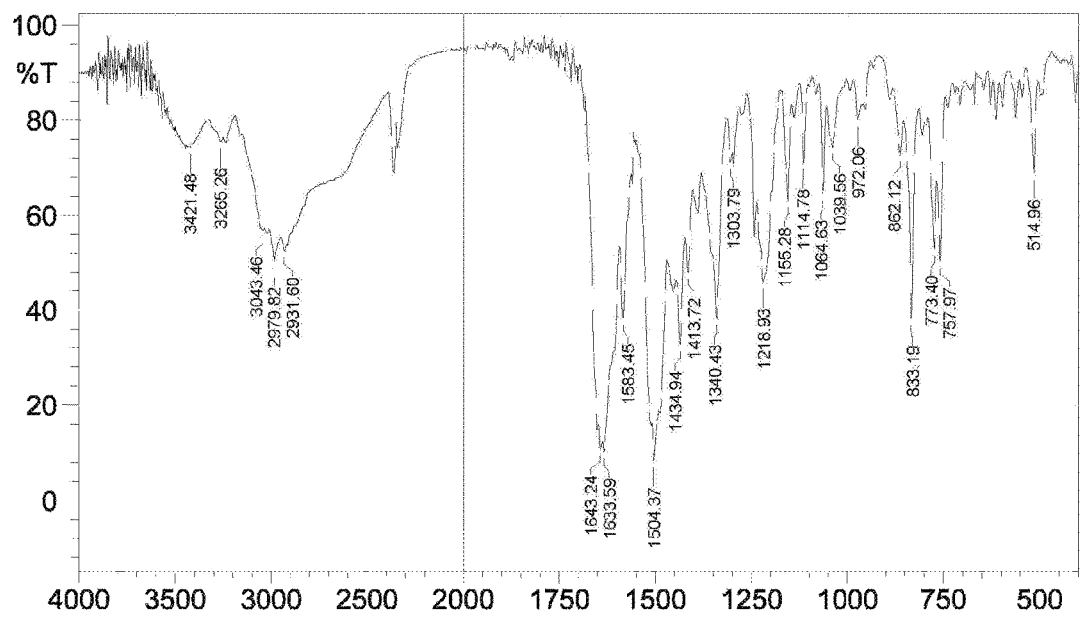

The thermogravimetry-differential thermal analysis atlas (TG-DTA) shows that crystalline form III has an endothermic peak at 218° C., and has an exothermic peak at 140° C., which are shown in FIG. 8. The infra-red spectrogram of crystalline form III shows that it has characteristic absorption peaks at 3421.48, 3265.26, 3043.46, 2979.82, 2931.60, 1643.24, 1633.59, 1583.45, 1504.37, 1434.94, 1413.72, 1340.43, 1303.79, 1218.93, 1155.28, 1114.78, 1064.63, 1039.56, 972.06, 862.12, 833.19, 773.40, 757.97 and 514.96 cm$^{-1}$. The infra-red spectrogram is shown in FIG. 9.

Embodiment 4 Revaprazan Hydrochloride Crystalline Form IV

Figure 10:
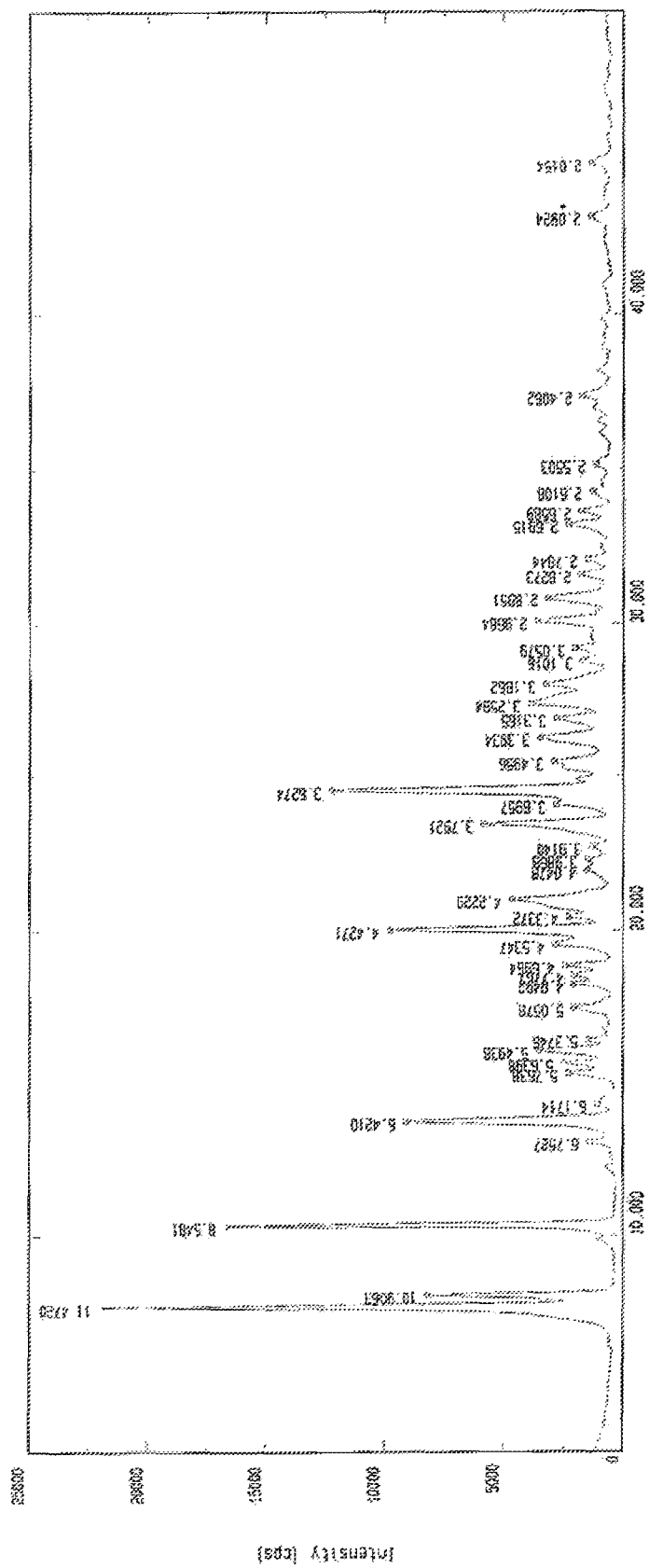

In the powder X-ray diffraction pattern of revaprazan hydrochloride crystalline form IV, 2θ, which is represented in degree, the characteristic diffraction peaks at 7.70±0.2, 10.34±0.2, 24.52±0.2, 20.04±0.2, 13.78±0.2. The specific powder X-ray diffraction data is shown in Table 24, and its powder X-ray diffraction pattern is shown in FIG. 10.

TABLE 24

Parameters of characteristic peaks of powder X-ray diffraction pattern of revaprazan hydrochloride crystalline form IV

| Serial Number | 2θ | d value | Relative intensity I/I⁰ |
|---|---|---|---|
| 1 | 7.700 | 11.4720 | 100 |
| 2 | 8.100 | 10.9063 | 37 |
| 3 | 10.340 | 8.5481 | 76 |
| 4 | 13.100 | 6.7527 | 6 |
| 5 | 13.780 | 6.4210 | 42 |
| 6 | 14.340 | 6.1714 | 5 |
| 7 | 15.360 | 5.7638 | 11 |
| 8 | 15.700 | 5.6398 | 11 |
| 9 | 16.120 | 5.4938 | 16 |
| 10 | 16.480 | 5.3746 | 7 |
| 11 | 17.520 | 5.0578 | 9 |
| 12 | 18.280 | 4.8492 | 9 |
| 13 | 18.560 | 4.7767 | 9 |
| 14 | 18.880 | 4.6964 | 11 |
| 15 | 19.560 | 4.5347 | 13 |
| 16 | 20.040 | 4.4271 | 45 |
| 17 | 20.460 | 4.3372 | 10 |
| 18 | 21.020 | 4.2229 | 21 |
| 19 | 21.940 | 4.0478 | 7 |
| 20 | 22.280 | 3.9868 | 7 |
| 21 | 22.700 | 3.9140 | 6 |
| 22 | 23.440 | 3.7921 | 27 |
| 23 | 24.060 | 3.6957 | 13 |
| 24 | 24.520 | 3.6274 | 56 |
| 25 | 25.460 | 3.4956 | 13 |
| 26 | 26.240 | 3.3934 | 16 |
| 27 | 26.860 | 3.3165 | 13 |
| 28 | 27.340 | 3.2594 | 18 |
| 29 | 27.980 | 3.1862 | 15 |

TABLE 24-continued

Parameters of characteristic peaks of powder X-ray diffraction pattern of revaprazan hydrochloride crystalline form IV

| Serial Number | 2θ | d value | Relative intensity I/I⁰ |
|---|---|---|---|
| 30 | 28.760 | 3.1016 | 8 |
| 31 | 29.180 | 3.0579 | 9 |
| 32 | 30.080 | 2.9684 | 16 |
| 33 | 30.860 | 2.8951 | 14 |
| 34 | 31.620 | 2.8273 | 8 |
| 35 | 32.120 | 2.7844 | 7 |
| 36 | 33.260 | 2.6915 | 11 |
| 37 | 33.680 | 2.6589 | 8 |
| 38 | 34.320 | 2.6108 | 6 |
| 39 | 35.160 | 2.5503 | 5 |
| 40 | 37.340 | 2.4062 | 8 |
| 41 | 43.200 | 2.0924 | 6 |
| 42 | 44.940 | 2.0154 | 6 |

Figure 11:
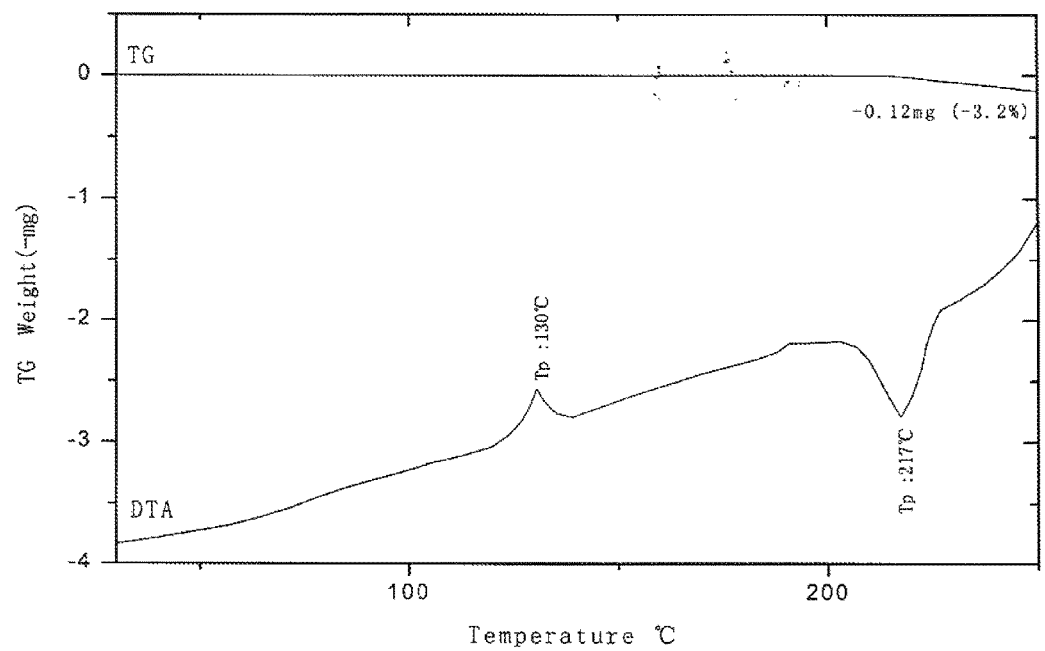
Figure 12:
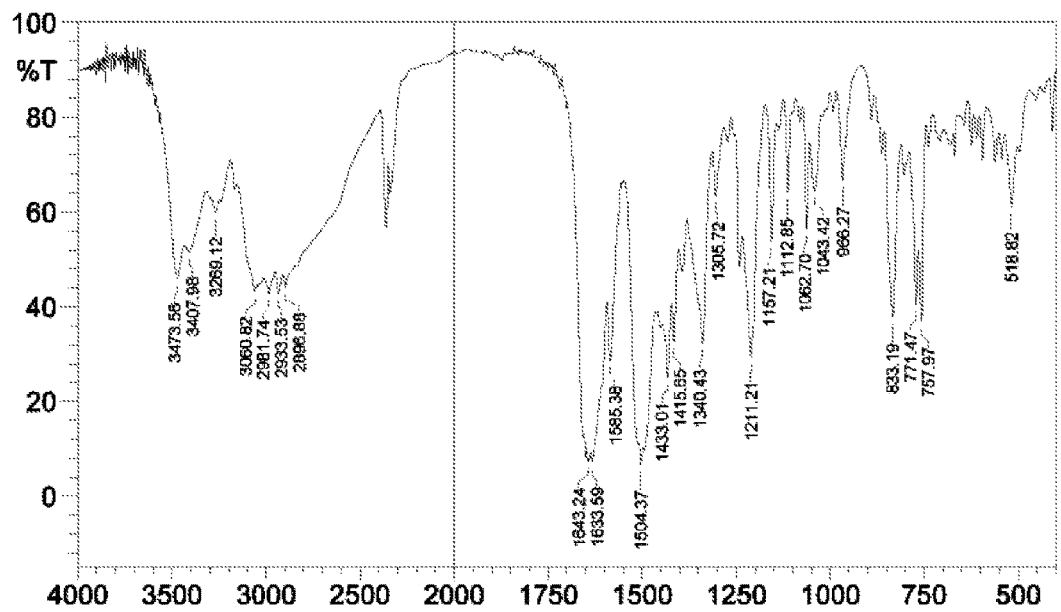

The thermogravimetry-differential thermal analysis atlas (TG-DTA) shows that crystalline form IV has an endothermic peak at 217° C., and has an exothermic peak at 130° C., which are shown in FIG. 11. The infra-red spectrogram of the crystalline form IV shows that there are characteristic absorption peaks at 3473.56, 3407.98, 3269.12, 3060.82, 2981.74, 2933.53, 2896.88, 1643.24, 1633.59, 1585.38, 1504.37, 1433.01, 1415.65, 1340.43, 1305.72, 1211.21, 1157.21, 1112.85, 1062.70, 1043.42, 966.27, 833.19, 771.47, 757.97 and 518.82 cm$^{-1}$. The infra-red spectrogram is shown in FIG. 12.

Embodiment 5 Revaprazan Hydrochloride Crystalline Form V

Figure 13:
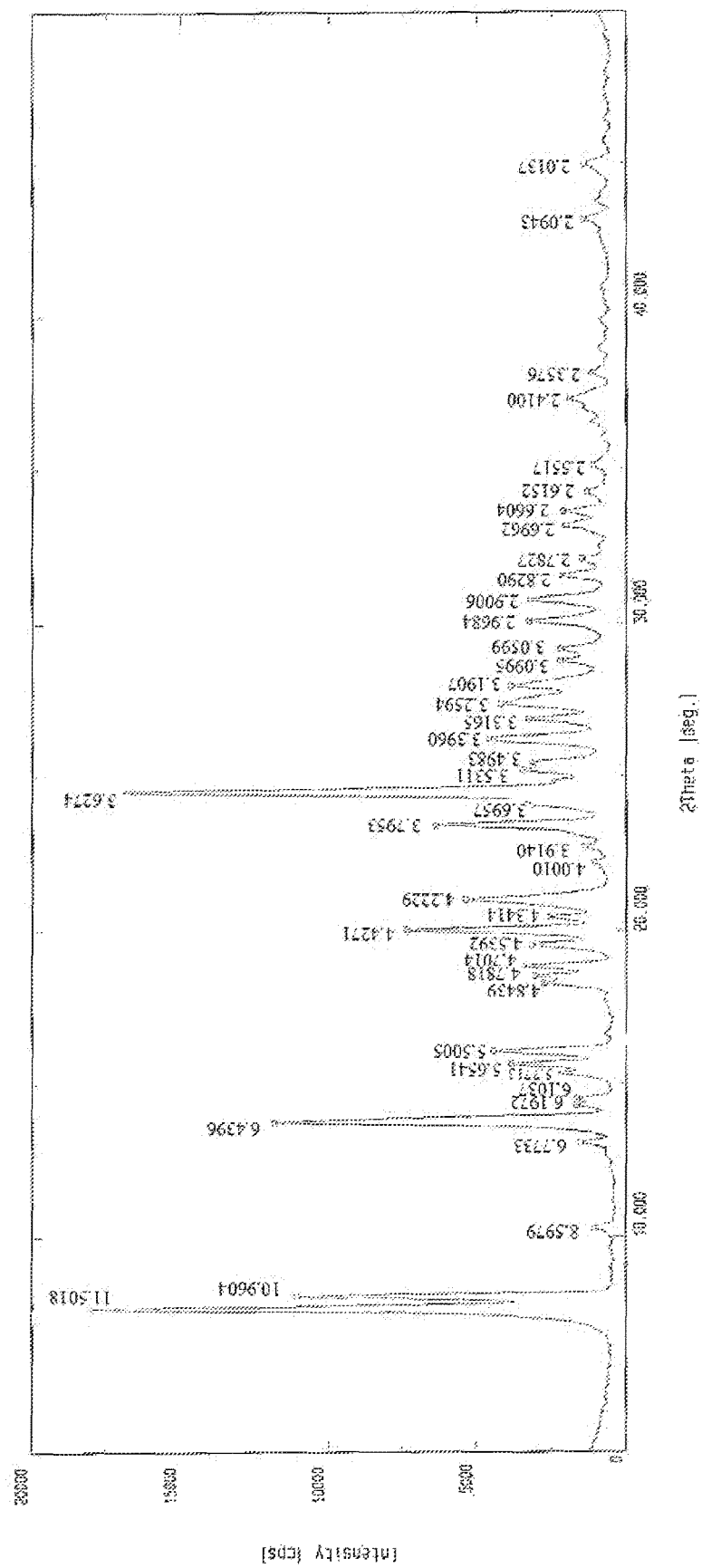

In the powder X-ray diffraction pattern, 2θ, which is represented in degree, the characteristic diffraction peaks at 7.68±0.2, 24.52±0.2, 13.74±0.2, 8.06±0.2, 19.54±0.2. The specific powder X-ray diffraction data is shown in Table 25, and its powder X-ray diffraction pattern is shown in FIG. 13.

TABLE 25

Parameters of characteristic peaks of powder X-ray diffraction pattern of revaprazan hydrochloride crystalline form V

| Serial Number | 2θ | d value | Relative intensity I/I⁰ |
|---|---|---|---|
| 1 | 7.680 | 11.5018 | 100 |
| 2 | 8.060 | 10.9604 | 62 |
| 3 | 10.280 | 8.5979 | 6 |
| 4 | 13.060 | 6.7733 | 9 |
| 5 | 13.740 | 6.4396 | 66 |
| 6 | 14.280 | 6.1972 | 9 |
| 7 | 14.500 | 6.1037 | 9 |
| 8 | 15.340 | 5.7713 | 13 |
| 9 | 15.660 | 5.6541 | 21 |
| 10 | 16.100 | 5.5005 | 25 |
| 11 | 18.300 | 4.8439 | 15 |
| 12 | 18.540 | 4.7818 | 17 |
| 13 | 18.860 | 4.7014 | 19 |
| 14 | 19.540 | 4.5392 | 18 |
| 15 | 20.040 | 4.4271 | 41 |
| 16 | 20.440 | 4.3414 | 14 |
| 17 | 21.020 | 4.2229 | 30 |
| 18 | 22.200 | 4.0010 | 6 |
| 19 | 22.700 | 3.9140 | 8 |
| 20 | 23.420 | 3.7953 | 35 |
| 21 | 24.060 | 3.6957 | 18 |
| 22 | 24.520 | 3.6274 | 96 |
| 23 | 25.200 | 3.5311 | 19 |
| 24 | 25.440 | 3.4983 | 18 |
| 25 | 26.220 | 3.3960 | 26 |

TABLE 25-continued

Parameters of characteristic peaks of powder X-ray diffraction pattern of revaprazan hydrochloride crystalline form V

| Serial Number | 2θ | d value | Relative intensity I/I⁰ |
|---|---|---|---|
| 26 | 26.860 | 3.3165 | 18 |
| 27 | 27.340 | 3.2594 | 23 |
| 28 | 27.940 | 3.1907 | 21 |
| 29 | 28.780 | 3.0995 | 12 |
| 30 | 29.160 | 3.0599 | 12 |
| 31 | 30.080 | 2.9684 | 18 |
| 32 | 30.800 | 2.9006 | 18 |
| 33 | 31.600 | 2.8290 | 12 |
| 34 | 32.140 | 2.7827 | 8 |
| 35 | 33.200 | 2.6962 | 11 |
| 36 | 33.660 | 2.6604 | 12 |
| 37 | 34.260 | 2.6152 | 7 |
| 38 | 35.140 | 2.5517 | 6 |
| 39 | 37.280 | 2.4100 | 11 |
| 40 | 38.140 | 2.3576 | 7 |
| 41 | 43.160 | 2.0943 | 8 |
| 42 | 44.980 | 2.0137 | 8 |

Figure 14:
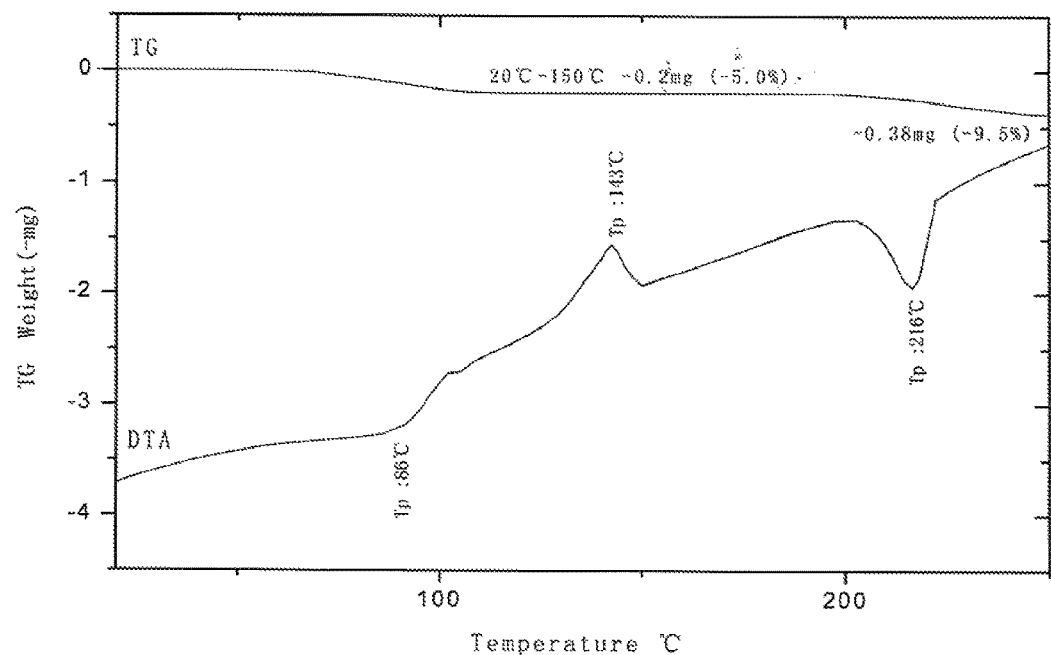
Figure 15:
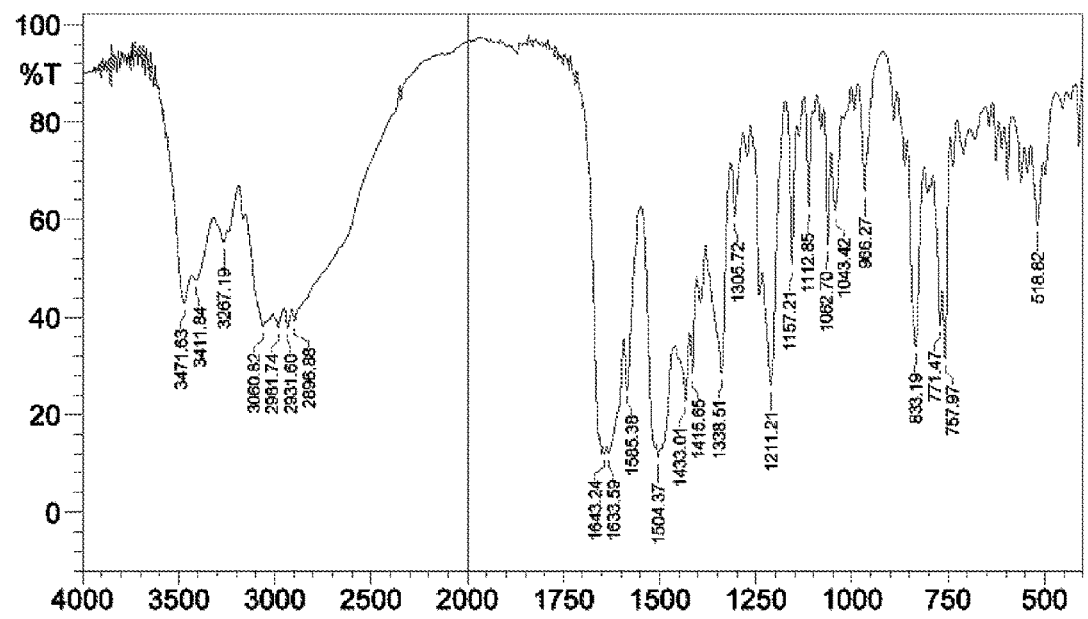

The thermogravimetry-differential thermal analysis atlas (TG-DTA) shows that crystalline form IV has an endothermic peak at 216° C., and has an exothermic peak at 143° C., which are shown in FIG. 14. The infra-red spectrogram of the crystalline form V shows that there are characteristic absorption peaks at 3471.63, 3411.84, 3267.19, 3060.82, 2981.74, 2931.60, 2896.88, 1643.24, 1633.59, 1585.38, 1504.37, 1433.01, 1415.65, 1338.51, 1305.72, 1211.21, 1157.21, 1112.85, 1062.70, 1043.42, 966.27, 833.19, 771.47, 757.97 and 518.82 cm$^{-1}$. The infra-red spectrogram is shown in FIG. 15.

EMBODIMENTS OF THE PREPARATION METHOD

Embodiment 1 Preparation of Revaprazan Hydrochloride Crystalline Form I 10 g of crude product of revaprazan hydrochloride is placed in a reaction flask, 30 g of 87% ethanol aqueous solution is added, under the protection of nitrogen, the mixture is stirred and heated until completely dissolved, after slight cooling, 0.1 g of activated carbon is added, reflux-decoloration is performed for 15 min, and the solution is filtered while hot and is cooled to 15° C. for crystallization under stirring. It is filtered and washed with 87% ethanol aqueous solution, and is dried to obtain the product (8.9 g).

Embodiment 2 Preparation of Revaprazan Hydrochloride Crystalline Form I 50 g of crude product of revaprazan hydrochloride is placed in a reaction flask, 250 g of 90% ethanol aqueous solution is added, under the protection of nitrogen, the mixture is stirred and heated until completely dissolved, after slight cooling, 0.5 g of activated carbon is added, reflux-decoloration is performed for 10 min, and the solution is filtered while hot and is cooled to 0° C. for crystallization under stirring. It is filtered and washed with 90% ethanol aqueous solution, and is dried to obtain the product (47.3 g).

Embodiment 3 Preparation of Revaprazan Hydrochloride Crystalline Form I 20 g of crude product of revaprazan hydrochloride is placed in a reaction flask, 200 g of 95% ethanol aqueous solution is added, under the protection of nitrogen, the mixture is stirred and heated until completely dissolved, after slight cooling, 0.2 g of activated carbon is added, reflux-decoloration is performed for 5 min, and the solution is filtered while hot and is cooled to 5° C. for crystallization under stirring. It is filtered and washed with 95% ethanol aqueous solution, and is dried to obtain the product (18.9 g).

Embodiment 4 Preparation of Revaprazan Hydrochloride Crystalline Form I 10 g of crude product of revaprazan hydrochloride is placed in a reaction flask, 150 g of 98% ethanol aqueous solution is added, the mixture is stirred and heated until completely dissolved, after slight cooling, 0.1 g of activated carbon is added, reflux-decoloration is performed for 15 min, and the solution is filtered while hot and is cooled to 10° C. for crystallization under stirring. It is filtered and washed with 98% ethanol aqueous solution, and is dried to obtain the product (9.3 g).

Embodiment 5 Preparation of Revaprazan Hydrochloride Crystalline Form I 5 g of crude product of revaprazan hydrochloride is placed in a reaction flask, and 100 g of anhydrous alcohol aqueous solution is added, the mixture is stirred and heated until completely dissolved, 0.1 g of activated carbon is added after slight cooling, reflux-decoloration is performed for 15 min, and the solution is filtered while hot and is cooled to 15° C. for crystallization under stirring. The crystals are filtered and washed with anhydrous alcohol aqueous solution, and are dried to obtain 4.6 g product.

Embodiment 6 Preparation of Revaprazan Hydrochloride Crystal Form II 20 g of crude product of revaprazan hydrochloride is placed in a reaction flask, and 200 g of anhydrous alcohol aqueous solution is added, the mixture is stirred and heated under the protection of nitrogen until completely dissolved, 0.2 g of activated carbon is added after slight cooling, reflux-decoloration is performed for 5 min, and the solution is filtered while hot and is cooled to 15° C. for crystallization under stirring. The crystals are filtered and washed with 85% anhydrous alcohol aqueous solution, and are dried to obtain 18.1 g product.

Embodiment 7 Preparation of Revaprazan Hydrochloride Crystal Form III 30 g of crude product of revaprazan hydrochloride is placed in a reaction flask, and 150 g of 75% anhydrous alcohol aqueous solution is added, the mixture is stirred and heated under the protection of nitrogen until completely dissolved, 0.3 g of activated carbon is added after slight cooling, reflux-decoloration is performed for 15 min, and the solution is filtered while hot and is cooled to 15° C. for crystallization under stirring. The crystals are filtered and washed with 75% anhydrous alcohol aqueous solution, and are dried to obtain 27.6 g product.

Embodiment 8 Preparation of Revaprazan Hydrochloride Crystal Form IV 30 g of crude product of revaprazan hydrochloride is placed in a reaction flask, and 300 g of 70% anhydrous alcohol aqueous solution is added, the mixture is stirred and heated until completely dissolved, 0.3 g of activated carbon is added after slight cooling, reflux-decoloration is performed for 5 min, and the solution is filtered while hot and is cooled to 15° C. for crystallization under stirring. The crystals are filtered and washed with 70% anhydrous alcohol aqueous solution, and is dried to obtain 27.1 g product of.

Embodiment 9 Preparation of Revaprazan Hydrochloride Crystal Form V 30 g of crude product of revaprazan hydrochloride is placed in a reaction flask, and 180 g of 50% anhydrous alcohol aqueous solution is added, the mixture is stirred and heated until completely dissolved under the protection of nitrogen, 0.3 g of activated carbon is added after slight cooling, reflux-decoloration is performed for 5 min, and the solution is filtered while hot and is cooled to 5° C. for crystallization under stirring. The crystals are filtered and washed with 50% anhydrous alcohol aqueous solution, and are dried to obtain 27.0 g product.

FORMULATION EMBODIMENTS

Embodiment 1

0.5 g of any one polymorph product of embodiments 1-5 is taken and is evenly mixed with 10.5 g of polyethylene glycol 6000, heating and melting are performed, the molten material is transferred into a dripper for dripping pills, the drug solution is dropwise added into 6-8° C. liquid paraffin, followed by deoiling, to obtain 400 dripping pills.

Embodiment 2

0.5 g of any one polymorph product of embodiments 1-5, 4.5 g of glucose, 0.9 g of sodium thiosulfate and 1 mL of distilled water are taken and mixed evenly, freeze-dried, and packaged in 500 ampoules, to obtain the final products.

Embodiment 3

0.5 g of any one polymorph product of embodiments 1-5, 5.5 g of mannitol, 0.9 g of calcium sodium edetate and 2 mL of distilled water are taken and mixed evenly, freeze-dried, and packaged in 300 ampoules, to obtain the final products.

Embodiment 4

0.5 g of any one polymorph product of embodiments 1-5, 50 g of starch and 50 g of sucrose are taken and evenly mixed, granulated and tabletted to obtain tablets.

Embodiment 5

0.5 g of any one polymorph product of embodiments 1-5, 50 g of starch and 50 g of sucrose are taken and mixed evenly, granulated and encapsulated to obtain capsules.

The invention claimed is:

1. A revaprazan hydrochloride polymorph, wherein, the melting point is 210-226° C.

2. The revaprazan hydrochloride polymorph of claim 1, wherein,
the revaprazan hydrochloride polymorph of which the melting point is 221-226° C. is revaprazan hydrochloride crystalline form I; or
the revaprazan hydrochloride polymorph of which the melting point is 218-222° C. is revaprazan hydrochloride crystalline form II; or
the revaprazan hydrochloride polymorph of which the melting point is 216-220° C. is revaprazan hydrochloride crystalline form III; or
the revaprazan hydrochloride polymorph of which the melting point is 215-219° C. is revaprazan hydrochloride crystalline form IV; or
the revaprazan hydrochloride polymorph of which the melting point is 210-218° C. is revaprazan hydrochloride crystalline form V.

3. The revaprazan hydrochloride polymorph of claim 2, wherein in the powder X-ray diffraction pattern of the revaprazan hydrochloride crystalline form I, 2θ, which is represented in degree with the characteristic diffraction peaks at 10.24±0.2, 21.92±0.2, 17.54±0.2, 26.70±0.2 and 20.72±0.2.

4. The revaprazan hydrochloride polymorph of claim 3, wherein in the powder X-ray diffraction pattern of the revaprazan hydrochloride crystalline form I, characteristic diffraction peaks of 2θ represented in degree are as follows:

| serial number | 2θ | d value | relative intensity I/I⁰ |
| --- | --- | --- | --- |
| 1 | 7.300 | 12.0996 | 15 |
| 2 | 10.240 | 8.6314 | 100 |
| 3 | 12.160 | 7.2725 | 28 |
| 4 | 13.240 | 6.6816 | 17 |
| 5 | 14.660 | 6.0374 | 5 |
| 6 | 16.300 | 5.4335 | 29 |
| 7 | 16.840 | 5.2605 | 19 |
| 8 | 17.540 | 5.0521 | 42 |
| 9 | 18.240 | 4.8597 | 4 |
| 10 | 19.580 | 4.5301 | 25 |
| 11 | 20.720 | 4.2833 | 32 |
| 12 | 21.920 | 4.0515 | 45 |
| 13 | 22.200 | 4.0010 | 25 |
| 14 | 22.480 | 3.9518 | 10 |
| 15 | 23.220 | 3.8275 | 17 |
| 16 | 24.240 | 3.6687 | 14 |
| 17 | 25.440 | 3.4983 | 24 |
| 18 | 25.920 | 3.4346 | 13 |
| 19 | 26.700 | 3.3360 | 33 |
| 20 | 27.980 | 3.1862 | 31 |
| 21 | 29.440 | 3.0315 | 17 |
| 22 | 31.160 | 2.8679 | 7 |
| 23 | 31.920 | 2.8014 | 7 |
| 24 | 33.040 | 2.7089 | 5 |
| 25 | 34.600 | 2.5903 | 6 |
| 26 | 36.300 | 2.4728 | 6 |
| 27 | 37.620 | 2.3890 | 7 |
| 28 | 39.680 | 2.2696 | 6. |

5. The revaprazan hydrochloride polymorph of claim 2, wherein the thermogravimetry-differential thermal analysis atlas TG-DTA of the revaprazan hydrochloride crystalline form I shows that there is an endothermic peak at 223° C.

6. The revaprazan hydrochloride polymorph of claim 2, wherein the infra-red spectrogram of the revaprazan hydrochloride crystalline form I shows that there are characteristic diffraction peaks at 3429.20, 3263.33, 2979.82, 2914.24, 1643.24, 1633.59, 1583.45, 1504.37, 1434.94, 1413.72, 1340.43, 1303.79, 1218.93, 1155.28, 1114.78, 1064.63, 1039.56, 972.06, 862.12, 833.19, 773.40, 757.97, and 514.96 cm$^{-1}$.

7. The revaprazan hydrochloride polymorph of claim 2, wherein in the powder X-ray diffraction pattern of revaprazan hydrochloride crystalline form II, the 2θ represented in degree with the characteristic diffraction peaks at 10.26±0.2, 24.48±0.2, 7.62±0.2, 21.94±0.2, 26.76±0.2 and 28.00±0.2; and/or the thermogravimetric-differential thermal analysis atlas TG-DTA of the revaprazan hydrochloride crystalline form II shows that there is an endothermic peak at 220° C. and an exothermic peak at 137° C.; and/or the infra-red spectrogram of the revaprazan hydrochloride polymorph shows that there are characteristic diffraction peaks at 3431.13, 3056.96, 2979.82, 2931.60, 1643.24, 1633.59, 1583.45, 1504.37, 1434.94, 1415.65, 1340.43, 1305.72, 1213.14, 1155.28, 1114.78, 1064.63, 1041.49, 972.06, 862.12, 833.19, 773.40, 757.97 and 514.96 cm$^{-1}$.

8. The revaprazan hydrochloride polymorph of claim 2, wherein in the powder X-ray diffraction pattern of the revaprazan hydrochloride crystalline form III, the 2θ represented in degree the characteristic diffraction peaks at 7.74±0.2, 24.42±0.2, 13.80±0.2, 7.38±0.2 and 25.62±0.2; and/or the thermogravimetric-differential thermal analysis atlas TG-DTA of the revaprazan hydrochloride crystalline form III shows that there is an endothermic peak at 218° C. and an exothermic peak at 140° C.; and/or the infra-red spectrogram of the revaprazan hydrochloride crystalline form III shows that there are characteristic diffraction peaks at 3421.48, 3265.26, 3043.46, 2979.82, 2931.60, 1643.24, 1633.59, 1583.45, 1504.37, 1434.94, 1413.72, 1340.43, 1303.79, 1218.93, 1155.28, 1114.78, 1064.63, 1039.56, 972.06, 862.12, 833.19, 773.40, 757.97 and 514.96 cm$^{-1}$.

9. The revaprazan hydrochloride polymorph of claim 2, wherein in the powder X-ray diffraction pattern of revaprazan hydrochloride crystalline form IV, the 2θ represented in degree with the characteristic diffraction peaks at 7.70±0.2, 10.34±0.2, 24.52±0.2, 20.04±0.2 and 13.78±0.2; and/or the thermogravimetric-differential thermal analysis atlas TG-DTA of the revaprazan hydrochloride crystalline form IV shows that there is an endothermic peak at 217° C. and an exothermic peak at 130° C.; and/or the infra-red spectrogram of the revaprazan hydrochloride polymorph IV shows that there are characteristic diffraction peaks at 3473.56, 3407.98, 3269.12, 3060.82, 2981.74, 2933.53, 2896.88, 1643.24, 1633.59, 1585.38, 1504.37, 1433.01, 1415.65, 1340.43, 1305.72, 1211.21, 1157.21, 1112.85, 1062.70, 1043.42, 966.27, 833.19, 771.47, 757.97 and 518.82 cm$^{-1}$.

10. The revaprazan hydrochloride polymorph of claim 2, wherein in the powder X-ray diffraction pattern of the revaprazan hydrochloride crystalline form V powder, the 2θ represented in degree with the characteristic diffraction peaks at 7.68±0.2, 24.52±0.2, 13.74±0.2, 8.06±0.2 and 19.54±0.2; and/or the thermogravimetric-differential thermal analysis atlas TG-DTA of the revaprazan hydrochloride crystalline form V shows that there is an endothermic peak at 216° C. and an exothermic peak at 143° C.; and/or the infra-red spectrogram of the revaprazan hydrochloride polymorph V shows that there are characteristic absorption peaks at 3471.63, 3411.84, 3267.19, 3060.82, 2981.74, 2931.60, 2896.88, 1643.24, 1633.59, 1585.38, 1504.37, 1433.01, 1415.65, 1338.51, 1305.72, 1211.21, 1157.21, 1112.85, 1062.70, 1043.42, 966.27, 833.19, 771.47, 757.97 and 518.82 cm$^{-1}$.

11. A formulation containing revaprazan hydrochloride polymorph, being composed of the revaprazan hydrochloride crystalline form claimed in claim 1 and pharmaceutically acceptable auxiliary materials.

12. A method of preparing the revaprazan hydrochloride polymorph of claim 1, comprising the following steps:
   (1) dissolving the revaprazan hydrochloride with water-containing alcohol;
   (2) adding activated carbon, refluxing for decolorization, filtering to obtain filtrate; and
   (3) cooling the filtrate, stirring and crystallizing, filtering, washing to obtain a solid, and drying to obtain the polymorph.

13. The method of preparing the revaprazan hydrochloride of claim 12, wherein the water-containing alcohol in step (1) is 87-98% ethanol and the obtained polymorph is revaprazan hydrochloride crystalline form I; or
   the water-containing alcohol in step (1) is 85% ethanol and the obtained polymorph is revaprazan hydrochloride crystalline form II; or
   the water-containing alcohol in step (1) is 75% ethanol and the obtained polymorph is revaprazan hydrochloride crystalline form III; or
   the water-containing alcohol in step (1) is 70% ethanol and the obtained polymorph is revaprazan hydrochloride crystalline form IV; or
   the water-containing alcohol in step (1) is 50% ethanol and the obtained polymorph is revaprazan hydrochloride crystalline form V.

14. A formulation containing revaprazan hydrochloride polymorph, being composed of the revaprazan hydrochloride crystalline form claimed in claim 2 and pharmaceutically acceptable auxiliary materials.

15. A formulation containing revaprazan hydrochloride polymorph, being composed of the revaprazan hydrochloride crystalline form claimed in claim 3 and pharmaceutically acceptable auxiliary materials.

16. A formulation containing revaprazan hydrochloride polymorph, being composed of the revaprazan hydrochloride crystalline form claimed in claim 4 and pharmaceutically acceptable auxiliary materials.

17. A formulation containing revaprazan hydrochloride polymorph, being composed of the revaprazan hydrochloride crystalline form claimed in claim 5 and pharmaceutically acceptable auxiliary materials.

18. A formulation containing revaprazan hydrochloride polymorph, being composed of the revaprazan hydrochloride crystalline form claimed in claim 6 and pharmaceutically acceptable auxiliary materials.

19. A formulation containing revaprazan hydrochloride polymorph, being composed of the revaprazan hydrochloride crystalline form claimed in claim 7 and pharmaceutically acceptable auxiliary materials.

20. A formulation containing revaprazan hydrochloride polymorph, being composed of the revaprazan hydrochloride crystalline form claimed in claim 1 and pharmaceutically acceptable auxiliary materials.

21. The method of preparing the revaprazan hydrochloride of claim 12, wherein the water-containing alcohol in step (1) is ethanol.

22. The method of preparing the revaprazan hydrochloride of claim 12, wherein the water-containing alcohol in step (1) is 90-98 ethanol.

23. The method of preparing the revaprazan hydrochloride of claim 12, wherein the revaprazan hydrochloride has yield which is from 90% to 95%.

* * * * *